United States Patent

La Thangue et al.

(10) Patent No.: US 7,348,407 B2
(45) Date of Patent: Mar. 25, 2008

(54) STRESS-RESPONSIVE ACTIVATOR OF P300 (STRAP) PROTEIN

(76) Inventors: Nicholas Barnie La Thangue, c/o Division of Biochemistry and Molecular Biology, Institute of Biomedical and Life Sciences, Davidson Building University of Glasgow, Glasgow, Strathclyde (GB) G12 8QQ; Constantinos Demonacos, c/o Division of Biochemistry and Molecular Biology, Institute of Biomedical and Life Sciences, Davidson Building University of Glasgow, Glasgow, Strathclyde (GB) G12 8QQ; Marija Krstic-Demonacos, c/o Division of Biochemistry and Molecular Biology, Institute of Biomedical and Life Sciences, Davidson Building University of Glasgow, Glasgow, Strathclyde (GB) G12 8QQ ( * ) Notice: Subject to any disclaimer, the term of this patent is extended or adjusted under 35 U.S.C. 154(b) by 219 days.

(21) Appl. No.: 10/471,573

(22) PCT Filed: Mar. 19, 2002

(86) PCT No.: PCT/GB02/01349

§ 371 (c)(1),
(2), (4) Date: Aug. 16, 2004

(87) PCT Pub. No.: WO02/074957

PCT Pub. Date: Sep. 26, 2002

(65) Prior Publication Data

US 2004/0260062 A1 Dec. 23, 2004

(30) Foreign Application Priority Data

Mar. 19, 2001 (GB) .................................. 0106782.6

(51) Int. Cl.
*C07K 14/46* (2006.01)
*C07H 21/04* (2006.01)
*C12N 15/63* (2006.01)
*C12N 5/10* (2006.01)
*C12P 21/00* (2006.01)
*A61K 38/17* (2006.01)

(52) U.S. Cl. .................. 530/350; 536/23.5; 435/320.1; 435/325; 435/70.1; 514/2

(58) Field of Classification Search ...................... None
See application file for complete search history.

(56) References Cited

FOREIGN PATENT DOCUMENTS

WO    WO 01/60860    8/2001

OTHER PUBLICATIONS

Demonacos, C. et al ., "A TPR motif Cofactor Contributes to p300 Activity in the p53 Response", Jul. 2001, Mol. Cell, vol. 8: pp. 71-84.*
Ngo, J. et al. Computational Complexity, Protein Structure Prediction, and the Levinthal Paradox, 1994, The Protein Folding Problem and Tertiary Structure Prediction, Merz et al. (eds.), Birkhauser Boston: Boston, MA, pp. 433 and 492-495.*
Rudinger, J. "Characteristics of the amino acids as components of a peptide hormone sequence", 1976, in Peptide Hormones, Parsons (ed.), University Park Press: Baltimore, MD, pp. 1-7.*
Shikama, N. et al., "A Novel Cofactor for p300 that Regulates the p53 Response", 1999, Mol. Cell, vol. 4: pp. 365-376.*
Demonacos Constantinos et al; "Transcriptional Control During the p53 Response"; Cell Biology International, vol. 25, No. 2, 2001, pp. A3-A4, XP008007026.
Demonacos et al; "A TPR Motif Cofactor Contributes to p300Activity in the p53 Response"; Molecular Cell, (Jul. 2001) 8 (1) 71-84, Xp001074287.
Shikama Noriko et al; "A Novel Cofactor for p300 That Regulates the p53 Response"; Molecular Cell, vol. 4, No. 1999, pp. 365-376, XP002217510.
Database EMBL Online, Mar. 9, 2001, NIH-MGC Project: "Mus Musculus, mRNA, Partial cds"; Database Accession No. BC003272; Xp002217511.
Database Swissprotein Online, Mar. 4, 2002, Mao et al; "Human TPRs Structural Domain Protein SEQ NO: 2"; Database Accession No. ABB04616, XP002217512.
Database Geneseq Online, Mar. 4, 2002; Mao et al; "Human TPRs Structural Domain Encoding cDNA SEQ ID NO: 1"; Database Accession No. ABA04247, XP002217513.
Database Genseq Online, Nov. 6, 2001, Ota et al: "Human Polypeptide, SEQ ID NO: 3623"; Database Accession No. AAM93700, XP002217514.
Database Genseq Online, Nov. 6, 2001, Ota et al: "Human Full-Length cDNA, seq id no: 3522"; Database Accession No. AAK94644, XP002217515.
Database Genseq Online, Sep. 16, 2002, Schlegel et al; "Human Prostate Expression Marker cDNA 29199"; Database Accession No. ABV29208; XP002217517.
Database Genseq Online, Jul. 27, 2001, Williams et al; cDNA Library Derived SEQ 1039; Database Accession No. AAH31105, XP002217516.

* cited by examiner

*Primary Examiner*—Sumesh Kaushal
*Assistant Examiner*—Michael Burkhart
(74) *Attorney, Agent, or Firm*—Nixon & Vanderhye P.C.

(57) ABSTRACT

The invention provides a protein which is a stress-responsive activator of the p300 protein, and nucleic acid sequences encoding the protein. The protein performs a key role in facilitating stress-responsive protein-protein interactions within the p300 co-activator complex. The STRAP protein facilitates the interaction of other proteins in the p300 complex, and is thus a target for assays for modulators of the complex.

11 Claims, 17 Drawing Sheets

FIGURE 1A

MMADEEEEAKHVLQKLQGLVDRLYCFRDSYFETHS
VEDAGRKQQDVQEEMEKTLQQMEEVLGSAQVEAQA
LMLKGKALNVTPDYSPEAEVLLSKAVKLEPELVEA
WNQLGEVYWKKGDVTSAHTCFSGALTHCKNKVSLQ
NLSMVLRQLQTDSGDEHSRHVMDSVRQAKLAVQMD
VLDGRSWYILGNAYLSLYFNTGQNPKISQQALSAY
AQAEKVDRKASSNPDLHLNRATLHKYEESYGEALE
GFSQAAALDPAWPEPQQREQQLLEFLSRLTSLLES
KGKTKPKKLQSMLGSLRPAHLGPCGDGRYQSASGQ
KMTLELKPLSTLQPGVNSGTVVLGKVVFSLTTEEK
VPFTFGLVDSDGPCYAVMVYNVVQSWGVLIGDSVA
IPEPNLRHHQIRHKGKDYSFSSVRVETPLLLVVNG
KPQNSSSQASATVASRPQCE

```
mouse   MMADEEEEAKHVLQKLQGLVDRLYCFRDSYFETHSVEDAGRKQQDVQEEMEKTLQQMEEV
human   MMADEEEEVKPILQKLQELVDQLYSFRDCYFETHSVEDAGRKQQDVRKEMEKTLQQMEEV
        ********.* :*** *:.*.****************::********* mouse   LGSAQVEAQALMLKGKALNVTPDYSPEAEVLLSKAVKLEPELVEAWNQLGEVYWKKGDVT
human   VGSVQGKAQVLMLTGKALNVTPDYSPKAEELLSKAVKLEPELVEAWNQLGEVYWKKGDVA
        :**.* :**.***.***********:** ****************************:

mouse   SAHTCFSGALTHCKNKVSLQNLSMVLRQLQTDSGDEHSRHVMDSVRQAKLAVQMDVLDGR
human   AAHTCFSGALTHCRNKVSLQNLSMVLRQLRTDTEDEHSHHVMDSVRQAKSAVQMDVHDGR
        :*********:***********:: **:****** ** * mouse   SWYILGNAYLSLYFNTGQNPKISQQALSAYAQAEKVDRKASSNPDLHLNRATLHKYEESY
human   SWYILGNSYLSLYFSTGQNPKISQQALSAYAQAEKVDRKASSNPDLHLNRATLHKYEESY
        *****:**.******************************************* mouse   GEALEGFSQAAALDPAWPEPQQREQQLLEFLSRLTSLLESKGKTKPKKLQSMLGSLRPAH
human   GEALEGFSRAAALDPAWPEPRQREQQLLEFLDRLTSLLESKGKVKTKKLQSMLGSLRPAH
        ******:*******.******.********.*.************** mouse   LGPCGDGRYQSASGQKMTLELKPLSTLQPGVNSGTVVLGKVVFSLTTEEKVPFTFGLVDS
human   LGPCSDGHYQSASGQKVTLELKPLSTLQPGVNSGAVILGKVVFSLTTEEKVPFTFGLVDS
        **.:******:**************:*:*********************** mouse   DGPCYAVMVYNVVQSWGVLIGDSVAIPEPNLRHHQIRHKGKDYSFSSVRVETPLLLVVNG
human   DGPCYAVMVYNIVQSWGVLIGDSVAIPEPNLRLHRIQHKGKDYSFSSVRVETPLLLVVNG
        *********:****************** *:*:********************** mouse   KPQNSSSQASATVASRPQCE
human   KPQGSSSQAVATVASRPQCE
        ***.***** **********
```

```
   ATGATGGCTGATGAAGAGGAAGAAGCGAAGCACGTCTTGCAGAAATTGCAGGGACTGGTGGATCG
   GCTCTACTGTTTTCGAGACAGTTACTTTGAGACACATAGTGTCGAAGATGCAGGACGGAAGCAGC
 5 AGGATGTACAGGAAGAGATGGAGAAGACCCTGCAGCAGATGGAGGAAGTACTCGGTTCTGCCCAG
   GTTGAGGCACAGGCTCTGATGCTGAAGGGGAAGGCACTGAATGTGACTCCTGATTATAGCCCTGA
   GGCCGAGGTGCTTCTCTCCAAGGCCGTGAAGCTGGAGCCTGAGCTGGTGGAAGCCTGGAACCAGC
   TGGGTGAGGTGTACTGGAAGAAAGGAGATGTCACATCTGCCCACACCTGCTTCTCAGGAGCCCTC
   ACCCACTGCAAGAACAAAGTCTCTCTGCAGAACTTGTCCATGGTGCTCCGCCAGCTGCAGACCGA
10 CTCTGGAGATGAACATTCTCGCCACGTCATGGACAGCGTCCGGCAGGCTAAGTTGGCCGTGCAGA
   TGGATGTCCTTGATGGCCGCTCCTGGTATATCCTGGGGAATGCATATCTTTCTCTTTATTTCAAT
   ACTGGCCAGAACCCTAAGATCTCCCAGCAAGCCCTCAGTGCCTATGCTCAAGCAGAGAAGGTGGA
   CAGGAAAGCATCTAGCAACCCTGACCTTCATCTCAACAGGGCGACGTTACATAAATATGAGGAGA
   GTTATGGGGAGGCCCTTGAGGGTTTCTCTCAGGCTGCAGCGCTGGACCCTGCGTGGCCAGAGCCC
15 CAGCAACGAGAACAGCAACTCTTGGAATTCCTCAGTAGGCTAACCAGCCTCCTGGAGAGCAAGGG
   GAAGACAAAGCCCAAGAAGCTGCAGAGCATGCTGGGAAGCTTGCGCCCAGCTCATCTGGGCCCCT
   GTGGTGATGGGCGCTATCAGTCGGCCTCTGGGCAGAAGATGACCCTGGAGCTTAAGCCACTGAGC
   ACCCTGCAGCCTGGTGTGAACAGTGGCACCGTGGTCCTGGGAAAGGTGGTGTTCAGCCTGACCAC
   AGAGGAGAAAGTCCCCTTCACGTTTGGCTTGGTAGATTCGGATGGTCCCTGCTATGCAGTGATGG
20 TGTATAATGTGGTGCAGAGCTGGGGAGTGCTCATCGGGGACTCTGTAGCTATTCCTGAGCCCAAC
   CTTCGGCATCATCAAATCCGGCACAAGGGAAAGGACTATTCCTTCTCCAGCGTGCGTGTGGAAAC
   GCCTCTTCTGCTGGTGGTGAATGGAAAGCCACAGAACTCCAGCAGTCAAGCCTCTGCCACAGTAG
   CTTCAAGGCCACAGTGTGAATGA
25
```

```
I    69- QAL M LK GK AL N VTPDYSPE A EVL L SK A VKLE P EL-102
II  103- VEA W NQ LG EV Y WKKGDVTS A HTC F SG A LTHC K NK-136
III 179- GRS W YI LG NA Y LSLYFNTG Q NPK I SQ Q ALSA Y AQ-212
IV  224- PDL H LN RA TL H KYEESYGE A LEG F SQ A AALD P AW-257
V   332- NSG T VV LG KV V FSLTTEEK V PFT F GL V DSDG P CY-365
VI  373- VQS W GV LI GD S VAIPEPNL R HHQ I RH K GKDY S FS-406

TPR consensus:
             W    LG    Y         A     F  A         P
```

STRESS-RESPONSIVE ACTIVATOR OF P300 (STRAP) PROTEIN

This application is the US national phase of international application PCT/GB02/01349 filed 19 Mar. 2002, which designated the US.

FIELD OF INVENTION

This invention relates to the isolation and characterisation of a novel polypeptide (Stress Responsive Activator of p53: STRAP) which is shown to interact with p300 and the p300 co-factor JMY in the p300 co-activator complex. This complex is involved in the regulation of the transcription of p53 target genes.

BACKGROUND OF INVENTION

The p53 protein is a stress-responsive transcription factor which is induced by a variety of stimuli that act through mechanisms that alter p53 half-life (Ko and Prives, 1997; Levine, 1997). It is encoded by a tumour suppressor gene that is frequently mutated in human cancer cells (Greenblat, 1994). In normal cells p53 exerts its function through the targeted sequence-specific activation of a number of different p53-responsive genes. These genes include waf1, bax, mdm2 and gadd45 which encode proteins that give rise to the physiological consequences of p53 activation, namely apoptosis or cell cycle arrest (Ko and Prives, 1997). p53 alleles isolated from tumour cells frequently harbour mutations that disrupt p53 DNA binding activity (Cho et al., 1994), underscoring the importance of transcription-related functions in mediating the effects of p53 tumour suppression.

The pathways through which p53 activity is regulated have been subject to intense study. The transcriptional activation domain of p53 is targeted by the MDM2 oncoprotein, which thereafter prevents p53 from activating transcription by hindering the interaction of p53 with the transcription apparatus (Oliner et al., 1993; Lin et al., 1994). In this respect, MDM2 can override the physiological effects of p53 response (Wu et al., 1993), and it is consistent with this idea that mdm2 is often seen to be aberrantly expressed in human tumour cells (Piette et al., 1997). A further consequence of the interaction between MDM2 and p53 is a down-regulation in the level of p53 protein, which is mediated in part through a ubiquitin-dependent pathway and requires the MDM2 E3 ligase (Haupt et al., 1997; Honda et al., 1997; Kubbutat et al., 1997).

Because p53 inactivation is associated with many human cancers, research has been directed at restoring p53 function, in order to provide a therapy for these cancers. p53 may also make normal cells sensitive to stress and recently, research has also been directed at the temporary inhibition of p53 (Komarova E. and Gudkov A. (1998) Seminars in Cancer Biology 8(5) 389-400). This inhibition may be useful in ameliorating the p53 induced side effects of cancer therapies such as radio-and chemo-therapy, which include hair loss and damage to the lymphoid and haematopoietic systems and the intestinal epithelia.

Adverse effects associated with the activation of P53 have also been described in other conditions including injury associated cellular stress (e.g. burns), diseases associated with fever, local hypoxia conditions associated with a deficient blood supply (e.g. stroke and ischaemia) and cell aging (e.g. fibroblast senescence). Suppression of p53 activity may therefore be useful in therapies related to these conditions.

A considerable body of evidence supports a role for the p300/CBP family of co-activators in p53-dependent transcription (Shikama et al., 1997). For example, p300/CBP proteins physically interact with the p53 activation domain, and dominant-negative derivatives of p300/CBP proteins can block p53 activity (Avantaggiati et al., 1997; Gu et al., 1997; Lill et al., 1997; Lee et al., 1998). Moreover, phosphorylation of the p53 activation domain during the stress response is believed to antagonise the interaction with MDM2, and possibly stabilise the interaction with p300/CBP proteins (Sheih et al., 1997; Giaccia and Kastan, 1998; Chehab et al., 2000; Shieh et al., 2000). However, p300/CBP proteins function as integral components of larger multi-component co-activator complexes, and a variety of co-factors that make up p300/CBP complexes have been identified (Shikama et al., 1997; Shiltz and Nakatani, 2000). Of considerable interest is the JMY co-factor, which is an integral component of the p300 co-activator complex that augments the transcriptional activity of p53, and enhances the level of the p53 response (Shikama et al., 1999). No other components of the p300 complex transcription have been characterised which are involved in regulating p53.

SUMMARY OF INVENTION

The present inventors have isolated and characterised a new component of the p300 co-activator complex, which has been termed STRAP.

STRAP is composed almost entirely of a tandem array of tetratricopeptide (TPR) motifs (Lamb et al 1995) and can interact with distinct components of the p300 co-activator complex, such as p300 and the p300 co-factor JMY. STRAP augments the association between p300 and JMY and can induce the p53 response, providing indication that STRAP plays a role in regulating the assembly of the p300 co-activator complex under stress conditions.

STRAP also undergoes a stress-responsive protein accumulation. The ability of STRAP to promote the interaction of co-factors within the p300 complex, combined with its response under cellular stress, endow STRAP with a critical role in regulating the p53 response. Taken together, these results identify a new and hitherto unexpected level of control, mediated at the point of stress-responsive co-activator control, in the cellular response to stress.

BRIEF DESCRIPTION OF THE FIGURES

FIG. 1 shows the primary amino acid sequence of murine STRAP (440 amino acid residues, FIG. 1A, SEQ ID NO:1), human STRAP (440 amino acids, FIG. 1B, SEQ ID NO:2), and the alignment of the two sequences (FIG. 1C).

FIG. 2 shows the cDNA nucleic acid sequence (SEQ ID NO:3) encoding the STRAP amino acid sequence shown in FIG. 1A (SEQ ID NO:1).

FIG. 4 shows an alignment of the sequence from the six TPR motifs (SEQ ID NOs:4-9) in STRAP. The eight consensus residues derived from the alignment are shown below. The residue number is indicated at each end of the TPR motif. The consensus TPR motif is taken from Blatch and Lässle (1999).

DETAILED DESCRIPTION OF INVENTION

Figure 3:
FIG. 3 shows a diagrammatic summary of the distribution of the six TPR motifs in STRAP (each TPR motif is indicated as I to VI and highlighted).

According to one aspect of the present invention there is provided an isolated nucleic acid molecule encoding a polypeptide which includes the amino acid sequence shown in FIG. 1A (SEQ ID NO:1) or 1B (SEQ ID NO:2). For convenience, the sequences are referred to herein as the sequence shown in FIG. 1, and reference to the sequence of FIG. 1 is intended to include both sequences unless specified explicitly to the contrary.

The coding sequence may be that shown included in FIG. 2 (SEQ ID NO:3) or it may be a mutant, variant, derivative or allele of the sequence shown. A mutant, variant, derivative or allele may differ from the sequence shown by a change which is one or more of addition, insertion, deletion and substitution of one or more nucleotides of the sequence shown. Changes to a nucleotide sequence may result in an amino acid change at the protein level, or not, as determined by the genetic code.

Thus, nucleic acid according to the present invention may include a sequence different from the sequence shown in FIG. 2 (SEQ ID NO:3) yet encode a polypeptide with the same amino acid sequence. The amino acid sequence shown in FIG. 1 (SEQ ID NO:1 or SEQ ID NO-2) consists of 440 residues.

Alternatively, the encoded polypeptide may comprise an amino acid sequence which differs by one or more amino acid residues from the amino acid sequence shown in FIG. 1 (SEQ ID NO:1 or SEQ ID NO:2). Nucleic acid encoding a polypeptide which is an amino acid sequence mutant, variant, derivative or allele of the sequence shown in FIG. 1 (SEQ ID NO:1 or SEQ ID NO:2) is further provided by the present invention. Such polypeptides are discussed below. Nucleic acid encoding such a polypeptide may show at the nucleotide sequence and/or encoded amino acid level greater than about 60% homology with the coding sequence shown in FIG. 2 (SEQ ID NO:3) and/or the amino acid sequence shown in FIG. 1 (SEQ ID NO:1 or SEQ ID NO:2), greater than about 70% homology, greater than about 80% homology, greater than about 90% homology or greater than about 95% homology.

For amino acid "homology", this may be understood to be similarity (according to the established principles of amino acid similarity, e.g. as determined using the algorithm GAP (Genetics Computer Group, Madison, Wis.) or identity. GAP uses the Needleman and Wunsch algorithm to align two complete sequences that maximizes the number of matches and minimizes the number of gaps. Generally, the default parameters are used, with a gap creation penalty=12 and gap extension penalty=4. Use of GAP may be preferred but other algorithms may be used, e.g. BLAST (which uses the method of Altschul et al. (1990) J. Mol. Biol. 215: 405-410), FASTA (which uses the method of Pearson and Lipman (1988) PNAS USA 85: 2444-2448), or the Smith-Waterman algorithm (Smith and Waterman (1981) J. Mol. Biol. 147: 195-197), generally employing default parameters.

Another method for determining the best overall match between an nucleotide or amino acid sequence of the present invention, or a portion thereof, and a query sequence is the use of the FASTDB computer program based on the algorithm of Brutlag et al (Comp. App. Biosci., 6; 237-245 (1990)). The program provides a global sequence alignment. The result of said global sequence alignment is in percent identity. Suitable parameters used in a FASTDB search of a DNA sequence to calculate percent identity are: Matrix=Unitary, k-tuple=4, Mismatch penalty=1, Joining Penalty=30, Randomization Group Length=0, Cutoff Score=1, Gap Penalty=5, Gap Size Penalty=0.05, and Window Size=500 or query sequence length in nucleotide bases, whichever is shorter. Suitable parameters to calculate percent identity and similarity of an amino acid alignment are: Matrix=PAM 150, k-tuple=2, Mismatch Penalty=1, Joining Penalty=20, Randomization Group Length=0, Cutoff Score=1, Gap Penalty=5, Gap Size Penalty=0.05, and Window Size=500 or query sequence length in nucleotide bases, whichever is shorter.

Use of either of the terms "homology" and "homologous" herein does not imply any necessary evolutionary relationship between compared sequences, in keeping for example with standard use of terms such as "homologous recombination" which merely requires that two nucleotide sequences are sufficiently similar to recombine under the appropriate conditions. Further discussion of polypeptides according to the present invention, which may be encoded by nucleic acid according to the present invention, is found below.

The present invention extends to nucleic acid that hybridizes with any one or more of the specific sequences disclosed herein under stringent conditions. Such nucleic acid may include other animal, for example fish (such as the Zebra fish), worm (such as *C. elegans*) and particularly mammalian (e.g. rat or rabbit, sheep, goat, pig, or primate particularly human) homologues of the STRAP gene. Such sequences may be obtained by making or obtaining cDNA libraries made from dividing cells or tissues or genomic DNA libraries from other animal species, and probing such libraries with probes comprising all or part of a nucleic acid of the invention under conditions of medium to high stringency.

Suitable conditions include, e.g. for detection of sequences that are about 80-90% identical suitable conditions include hybridization overnight at 42° C. in 0.25M Na2HPO4, pH 7.2, 6.5% SDS, 10% dextran sulfate and a final wash at 55° C. in 0.1×SSC, 0.1% SDS. For detection of sequences that are greater than about 90% identical, suitable conditions include hybridization overnight at 65° C. in 0.25M Na2HPO4, pH 7.2, 6.5% SDS, 10% dextran sulfate and a final wash at 60° C. in 0.1×SSC, 0.1% SDS.

A variant form of a nucleic acid molecule may contain one or more insertions, deletions, substitutions and/or additions of one or more nucleotides compared with the wild-type sequence (such as shown in FIG. 2(SEQ ID NO:3)) which may or may not disrupt the gene function. Differences at the nucleic acid level are not necessarily reflected by a difference in the amino acid sequence of the encoded polypeptide. However, a mutation or other difference in a gene may result in a frame-shift or stop codon, which could seriously affect the nature of the polypeptide produced (if any), or a point mutation or gross mutational change to the encoded polypeptide, including insertion, deletion, substitution and/or addition of one or more amino acids or regions in the polypeptide. A mutation in a promoter sequence or other regulatory region may prevent or reduce expression from the gene or affect the processing or stability of the mRNA transcript. For instance, a sequence alteration may affect splicing of mRNA.

Generally, nucleic acid according to the present invention is provided as an isolate, in isolated and/or purified form, or free or substantially free of material with which it is naturally associated, such as free or substantially free of nucleic acid flanking the gene in the human genome, except possibly one or more regulatory sequence(s) for expression. Nucleic acid may be wholly or partially synthetic and may include genomic DNA, cDNA or RNA. The coding sequence shown herein is a DNA sequence. Where nucleic acid according to the invention includes RNA, reference to the sequence shown should be construed as encompassing reference to the RNA equivalent, with U substituted for T.

Nucleic acid may be provided as part of a replicable vector, and also provided by the present invention are a vector including nucleic acid as set out above, particularly any expression vector from which the encoded polypeptide can be expressed under appropriate conditions, and a host cell containing any such vector or nucleic acid. An expression vector in this context is a nucleic acid molecule including nucleic acid encoding a polypeptide of interest and appropriate regulatory sequences for expression of the polypeptide, in an in vitro expression system, e.g. reticulocyte lysate, or in vivo, e.g. in eukaryotic cells such as COS or CHO cells or in prokaryotic cells such as *E. coli*. This is discussed further below.

The nucleic acid sequence provided in accordance with the present invention is also useful in methods for identifying and/or obtaining nucleic acid of interest (and which may be according to the present invention) in a test sample, for example, homologues of the STRAP nucleotide sequence as described above.

A method of identifying and/or obtaining nucleic acid of interest may include hybridisation of a probe having the sequence shown in FIG. 2 (SEQ ID NO:3), or a complementary sequence, to target nucleic acid.

Hybridisation is generally followed by identification of successful hybridisation and isolation of nucleic acid which has hybridised to the probe, which may involve one or more steps of PCR. It will not usually be necessary to use a probe with the complete sequence shown in any of these figures. Shorter fragments, particularly fragments with a sequence encoding the conserved TPR motifs may be used. Suitable sequences may include sequences encoding one or more of the TPR motifs shown in FIG. 4 (SEQ ID NOs:4-9).

Nucleic acids encoding or associated with the STRAP gene may also be used in methods of detecting the presence or absence of said gene in a human or non-human mammalian subject, said method comprising;

(a) bringing a sample of nucleic acid from said subject into contact, under hybridizing conditions, with a polynucleotide of the invention; and (b) determining whether said polynucleotide has been able to hybridize to a homologous sequence in said nucleic acid.

The method may be performed using a polynucleotide primer suitable for use in a polymerase chain reaction (PCR), and the determining may be performed in conjunction with a second primer using PCR such that a portion of the STRAP gene is amplified.

In one embodiment, the sample nucleic acid may be in the form of whole chromosomes, for example as a metaphase spread. The nucleic acid probe or primer of the invention may be labelled with a fluorescent label to detect the chromosomal location of a STRAP gene in the spread.

In some instances, the determining step may include determining the sequence of the STRAP gene, when present, in the nucleic acid sample. As one alternative, restriction length fragment polymorphisms associated with the gene may be established and the assay performed with a sample which has been digested with a restriction enzyme. Another method of determining is via PCR length polymorphisms, for example through variation in the sizes of introns. Other specific means of determining hybridization are well known and routine in the art and may also be used.

As well as determining the presence of polymorphisms or mutations in the STRAP sequence, the probes may also be used to determine whether mRNA encoding the STRAP gene is present in a cell or tissue.

Nucleic acid according to the present invention is obtainable using one or more oligonucleotide probes or primers designed to hybridise with one or more fragments of the nucleic acid sequence shown in any of the figures, particularly fragments of relatively rare sequence, based on codon usage or statistical analysis. A primer designed to hybridise with a fragment of the nucleic acid sequence shown in any of the figures may be used in conjunction with one or more oligonucleotides designed to hybridise to a sequence in a cloning vector within which target nucleic acid has been cloned, or in so-called "RACE" (rapid amplification of cDNA ends) in which cDNA's in a library are ligated to an oligonucleotide linker and PCR is performed using a primer which hybridises with a sequence shown and a primer which hybridises to the oligonucleotide linker.

Nucleic acid isolated and/or purified from one or more cells (e.g. human) or a nucleic acid library derived from nucleic acid isolated and/or purified from cells (e.g. a cDNA library derived from mRNA isolated from the cells), may be probed under conditions for selective hybridisation and/or subjected to a specific nucleic acid amplification reaction such as the polymerase chain reaction (PCR) (reviewed for instance in "PCR protocols; A Guide to Methods and Applications", Eds. Innis et al, 1990, Academic Press, New York, Mullis et al, Cold Spring Harbor Symp. Quant. Biol., 51:263, (1987), Ehrlich (ed), PCR technology, Stockton Press, NY, 1989, and Ehrlich et al, Science, 252:1643-1650, (1991)). PCR comprises steps of denaturation of template nucleic acid (if double-stranded), annealing of primer to target, and polymerization. The nucleic acid probed or used as template in the amplification reaction may be genomic DNA, cDNA or RNA. Other specific nucleic acid amplification techniques include strand displacement activation, the Qβ replicase system, the repair chain reaction, the ligase chain reaction and ligation activated transcription. For convenience, and because it is generally preferred, the term PCR is used herein in contexts where other nucleic acid amplification techniques may be applied by those skilled in the art. Unless the context requires otherwise, reference to PCR should be taken to cover use of any suitable nucleic acid amplification reaction available in the art.

In the context of cloning, it may be necessary for one or more gene fragments to be ligated to generate a full-length coding sequence. Also, where a full-length encoding nucleic acid molecule has not been obtained, a smaller molecule representing part of the full molecule, may be used to obtain full-length clones. Inserts may be prepared from partial cDNA clones and used to screen cDNA libraries. The full-length clones isolated may be subcloned into expression vectors and activity assayed by transfection into suitable host cells, e.g. with a reporter plasmid.

A method may include hybridisation of one or more (e.g. two) probes or primers to target nucleic acid. Where the nucleic acid is double-stranded DNA, hybridisation will generally be preceded by denaturation to produce single-stranded DNA. The hybridisation may be as part of a PCR procedure, or as part of a probing procedure not involving PCR. An example procedure would be a combination of PCR and low stringency hybridisation. A screening procedure, chosen from the many available to those skilled in the art, is used to identify successful hybridisation events and isolated hybridised nucleic acid.

Binding of a probe to target nucleic acid (e.g. DNA) may be measured using any of a variety of techniques at the disposal of those skilled in the art. For instance, probes may be radioactively, fluorescently or enzymatically labelled. Other methods not employing labelling of probe include examination of restriction fragment length polymorphisms, amplification using PCR, RN'ase cleavage and allele specific oligonucleotide probing. Probing may employ the standard Southern blotting technique. For instance, DNA may be extracted from cells and digested with different restriction enzymes. Restriction fragments may then be separated by electrophoresis on an agarose gel, before denaturation and transfer to a nitrocellulose filter. Labelled probe may be hybridised to the DNA fragments on the filter and binding determined. DNA for probing may be prepared from RNA preparations from cells.

Preliminary experiments may be performed by hybridising various probes under low stringency conditions to Southern blots of DNA digested with restriction enzymes. Suitable conditions would be achieved when a large number of hybridising fragments were obtained while the background hybridisation was low. Using these conditions nucleic acid libraries, e.g. cDNA libraries representative of expressed sequences, may be searched. Those skilled in the art are well able to employ suitable conditions of the desired stringency for selective hybridisation, taking into account factors such as oligonucleotide length and base composition, temperature and so on. On the basis of amino acid sequence information, oligonucleotide probes or primers may be designed, taking into account the degeneracy of the genetic code, and, where appropriate, codon usage of the organism from which the candidate nucleic acid is derived.

An oligonucleotide for use in nucleic acid amplification may have about 10 or fewer codons (e.g. 6, 7 or 8), i.e. be about 30 or fewer nucleotides in length (e.g. 18, 21 or 24). Generally specific primers are upwards of 14 nucleotides in length, but need not be than 18-20. Those skilled in the art are well versed in the design of primers for use processes such as PCR. Various techniques for synthesizing oligonucleotide primers are well known in the art, including phosphotriester and phosphodiester synthesis methods.

Preferred amino acid sequences suitable for use in the design of probes or PCR primers may include sequences conserved (completely, substantially or partly) encoding the TPR motifs.

A further aspect of the present invention provides an oligonucleotide or polynucleotide fragment of the nucleotide sequence shown in any of the figures herein providing nucleic acid according to the present invention, or a complementary sequence, in particular for use in a method of obtaining and/or screening nucleic acid. A sequence may differ from any of the sequences shown by addition, substitution, insertion or deletion of one or more nucleotides, but preferably without abolition of ability to hybridise selectively with nucleic acid in accordance with the present invention, that is wherein the degree of similarity of the oligonucleotide or polynucleotide with one of the sequences given is sufficiently high.

In some preferred embodiments, oligonucleotides according to the present invention that are fragments of any of the sequences shown, are at least about 10 nucleotides in length, more preferably at least about 15 nucleotides in length, more preferably at least about 20 nucleotides in length. Such fragments themselves individually represent aspects of the present invention. Fragments and other oligonucleotides may be used as primers or probes as discussed.

Further embodiments of oligonucleotides according to the present invention are anti-sense oligonucleotide sequences based on the nucleic acid sequences described herein. Anti-sense oligonucleotides may be designed to hybridise to the complementary sequence of nucleic acid, pre-mRNA or mature mRNA, interfering with the production of polypeptide encoded by a given DNA sequence (e.g. either native polypeptide or a mutant form thereof), so that its expression is reduce or prevented altogether. Anti-sense techniques may be used to target a coding sequence, a control sequence of a gene, e.g. in the 5' flanking sequence, whereby the antisense oligonucleotides can interfere with control sequences. Antisense oligonucleotides may be DNA or RNA and may be of around 14-23 nucleotides, particularly around 15-18 nucleotides, in length. The construction of antisense sequences and their use is described in Peyman and Ulman, Chemical Reviews, 90:543-584, (1990), and Crooke, Ann. Rev. Pharmacol. Toxicol., 32:329-376, (1992).

Any of the sequences disclosed in the figures herein may be used to construct a probe for use in identification and isolation of a promoter from a genomic library containing a genomic STRAP gene. Techniques and conditions for such probing are well known in the art and are discussed elsewhere herein. To find minimal elements or motifs responsible for stress and/or developmental regulation, restriction enzyme or nucleases may be used to digest a nucleic acid molecule, followed by an appropriate assay (for example using a reporter gene such as luciferase) to determine the sequence required.

A further aspect of the present invention provides a nucleic acid molecule as described herein operably linked to a promoter or other regulatory sequence.

By "promoter" is meant a sequence of nucleotides from which transcription may be initiated of DNA operably linked downstream (i.e. in the 3' direction on the sense strand of double-stranded DNA).

"Operably linked" means joined as part of the same nucleic acid molecule, suitably positioned and oriented for transcription to be initiated from the promoter. DNA operably linked to a promoter is "under transcriptional initiation regulation" of the promoter.

A further aspect of the present invention provides a polypeptide which has the amino acid sequence shown in FIG. 1 (SEQ ID NO:1 or SEQ ID NO:2), which may be in isolated and/or purified form, free or substantially free of material with which it is naturally associated, such as other polypeptides. If produced by expression in a prokaryotic cell) the polypeptide may be lacking in native glycosylation, e.g. unglycosylated. Polypeptides may of course be formulated with diluents or adjuvants and still for practical purposes be isolated—for example the polypeptides will normally be mixed with gelatin or other carriers if used to coat microtitre plates for use in immunoassays. Polypeptides may be phosphorylated and/or acetylated.

Such a polypeptide is termed a STRAP polypeptide. This term also includes amino acid sequence variants, alleles, derivatives and mutants as well as active portions and fragments thereof.

The invention further provides active portions and fragments which comprises an epitope of said polypeptide.

Unless otherwise specified below, such portions and fragments are also referred to as a polypeptide of the present invention.

Polypeptides which are amino acid sequence variants, alleles, derivatives or mutants are also provided by the present invention. A polypeptide which is a variant, allele, derivative or mutant may have an amino acid sequence which differs from that given in a figure herein by one or more of addition, substitution, deletion and insertion of one or more amino acids. Preferred such polypeptides have STRAP function, that is to say have one or more of the following properties: immunological cross-reactivity with an antibody reactive the polypeptide for which the sequence is given in a figure herein; sharing an epitope with the polypeptide for which the amino acid sequence is shown in a figure herein (as determined for example by immunological cross-reactivity between the two polypeptides); a biological activity which is inhibited by an antibody raised against the polypeptide whose sequence is shown in a figure herein; ability to bind with p300 and/or JMY. Alteration of sequence may change the nature and/or level of activity and/or stability of the STRAP polypeptide.

Polypeptides of the invention may be modified for example by the addition of histidine residues to assist their purification or by the addition of a signal sequence to promote their secretion from a cell.

A polypeptide which is an amino acid sequence variant, allele, derivative or mutant of the amino acid sequence shown in a figure herein may comprise an amino acid sequence which shares greater than about 35% sequence identity with the sequence shown, greater than about 40%, greater than about 50%, greater than about 60%, greater than about 70%, greater than about 80%, greater than about 90% or greater than about 95%. The sequence may share greater than about 60% similarity, greater than about 70% similarity, greater than about 80% similarity or greater than about 90% similarity with the amino acid sequence shown in the relevant figure.

Amino acid similarity is generally defined with reference to the algorithm GAP (Genetics Computer Group, Madison, Wis.) as noted above, or the TBLASTN program, of Altschul et al. (1990) J. Mol. Biol. 215: 403-10. Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine. Particular amino acid sequence variants may differ from that shown in a figure herein by insertion, addition, substitution or deletion of 1 amino acid, 2, 3, 4, 5-10, 10-20 20-30, 30-50, 50-100, 100-150, or more than 150 amino acids.

Sequence comparison may be made over the full-length of the relevant sequence shown herein, or may more preferably be over a contiguous sequence of about or greater than about 20, 25, 30, 33, 40, 50, 67, 133, 167, 200, 233, 267, 300, 333, 400, or more amino acids, compared with the relevant amino acid sequence as the case may be.

Preferred such polypeptides include those which are encoded by the STRAP gene of other mammals, particularly primates and most particularly man, as well as fragments of such polypeptides, such fragments being those as defined above. The primary sequence of the STRAP protein will be substantially similar to that of FIG. 1 (SEQ ID NO:1 or SEQ ID NO:2) and may be determined by routine techniques available to those of skill in the art. In essence, such techniques comprise using polynucleotides of the present invention as probes to recover and to determine the sequence of the STRAP gene in other species. Human STRAP is shown in FIG. 1B (SEQ ID NO:2), and was obtained in the light of the present invention by analysis of publicly available sequence databases. The databases do not identify that this protein as such, nor identify the function that is disclosed herein.

A wide variety of techniques are available for this, for example PCR amplification and cloning of the gene using a suitable source of mRNA (e.g. from an embryo or an actively dividing differentiated or tumour cell), or by methods comprising obtaining a cDNA library from the mammal, e.g a cDNA library from one of the above-mentioned sources, probing said library with a polynucleotide of the invention under stringent conditions, and recovering a cDNA encoding all or part of the STRAP protein of that mammal. Where a partial cDNA is obtained, the full length coding sequence may be determined by primer extension techniques.

The present invention also includes peptides which include or consist of fragments of a polypeptide of the invention.

The present inventors have also identified regions in the JMY and p300 sequence which interact with STRAP. A peptide consisting of such a region and nucleic acid encoding such a peptide are further aspects of the present invention.

Regions of JMY which interact with STRAP include residues 683 to 983 and regions of p300 which interact with STRAP include residues 1 to 595 and residues 1572 to 1921. The sequence of JMY is available as GenBank accession no. AAF 17555 and the sequence of p300 available as GenBank accession number XP010013.

"p300" refers to a family member of the p300/CBP family of co-activators which have histone acetyltransferase activity p300 is described for example by Eckner et al, 1994 and CBP by Bannister and Kouzarides, 1996. For the purposes of the present invention, reference to "p300" or "p300 polypeptide" refers to human allelic and synthetic variants of p300 or CBP, and to other mammalian variants and allelic and synthetic variants thereof, as well as fragments of said human and mammalian forms of p300 or CBP. Synthetic variants include those which have at least 80%, preferably at least 90%, homology to p300. More preferably such variants correspond to the sequence of p300 but have one or more, e.g. from 1 to 10, such as from 1 to 5, substitutions, deletions or insertions of amino acids. Fragments of p300 and its variants are preferably at least 20, more preferably at least 50 and most preferably at least 200 amino acids in size. The p300 molecule will however retain the ability to physically associate in vivo with STRAP.

Preferably, the p300 used in assays of the present invention will also retain the ability to interact with the tumour suppressor molecule p53, as described in the accompanying examples and by Lill et al, 1997.

For the purposes of the present invention, the precise form and structure of a p300 protein or fragment thereof may be varied by those of skill in the art, having regard to the particular assay format to be used.

"JMY" refers to any family member of the JMY family of co-activators which bind the p300/CBP co-activator complex and are disclosed in PCT/GB98/03152. For the purposes of the present invention, reference to "JMY" or "JMY polypeptide" refers to human allelic and synthetic variants of JMY, and to other mammalian variants and allelic and synthetic variants thereof, as well as fragments of said human and mammalian forms of JMY. Synthetic variants include those which have at least 80%, preferably at least 90%, homology to JMY. More preferably such variants correspond to the sequence of JMY but have one or more, e.g. from 1 to 10, such as from 1 to 5, substitutions, deletions or insertions of amino acids. Fragments of JMY and its variants are preferably at least 20, more preferably at least 50 and most preferably at least 200 amino acids in size. The JMY molecule will however retain the ability to physically associate in vivo with STRAP and/or p300.

For the purposes of the present invention, the precise form and structure of a JMY protein or fragment thereof may be varied by those of skill in the art, having regard to the particular assay format to be used.

"p53" refers to the tumour suppressor gene or its encoded amino acid sequence of as reported, for example, by Matlashewski et al (EMBO J. 13; 3257-62, 1984) or Lamb and Crawford (Mol. Cell. Biol. 5; 1379-85, 1986). These sequences are available on Genbank. Wild-type human p53 protein includes a proline/arginine polymorphism at amino acid 72, reflecting a corresponding polymorphism in the gene.

The skilled person can use the techniques described herein and others well known in the art to produce large amounts of peptides, for instance by expression from encoding nucleic acid.

Peptides can also be generated wholly or partly by chemical synthesis. The compounds of the present invention can be readily prepared according to well-established, standard liquid or, preferably, solid-phase peptide synthesis methods, general descriptions of which are broadly available (see, for example, in J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, New York (1984); and Applied Biosystems 430A Users Manual, ABI Inc., Foster City, Calif.).

The present invention also includes active portions, fragments, derivatives and functional mimetics of the polypeptides of the invention. An "active portion" of a polypeptide means a peptide which is less than said full length polypeptide, but which retains a biological activity, such as binding to p300 and/or JMY. Thus an active portion of the STRAP polypeptide may include amino acids 1 to 123 or amino acids 123 to 205 which bind JMY and/or may include amino acids 206 to 440, which bind p300. Such an active fragment may be included as part of a fusion protein, e.g. including a binding portion for a different ligand which may confer on the molecule a different binding specificity.

Active portions may also include those which are phosphorylated and/or acetylated, particularly in a cell-cycle specific manner.

A "fragment" of a polypeptide generally means a stretch of amino acid residues of at least about five contiguous amino acids, often at least about seven contiguous amino acids, typically at least about nine contiguous amino acids, more preferably at least about 13 contiguous amino acids, and, more preferably, at least about 20 to 30 or more contiguous amino acids. Fragments of the STRAP polypeptide sequence may include antigenic determinants or epitopes useful for raising antibodies to a portion of the amino acid sequence. Alanine scans are commonly used to find and refine peptide motifs within polypeptides, this involving the systematic replacement of each residue in turn with the amino acid alanine, followed by an assessment of biological activity.

Preferred fragments of STRAP include those which contain any of the following amino acid sequences shown in FIG. 1 (SEQ ID NO: 1 or SEQ ID NO:2): residues 1 to 123, residues 122 to 205, residues 206 to 440, which may be used for instance in raising or isolating antibodies. Variant and derivative peptides, peptides which have an amino acid sequence which differs from one of these sequences by way of addition, insertion, deletion or substitution of one or more amino acids are also provided by the present invention, generally with the proviso that the variant or derivative peptide is bound by an antibody or other specific binding member which binds one of the peptides whose sequence is shown. A peptide which is a variant or derivative of one of the shown peptides may compete with the shown peptide for binding to a specific binding member, such as an antibody or antigen-binding fragment thereof.

Where additional amino acids are included in a peptide, these may be heterologous or foreign to the polypeptide of the invention, and the peptide may be about 20, 25, 30 or 35 amino acids in length. A peptide according to this aspect may be included within a larger fusion protein, particularly where the peptide is fused to a non-STRAP (i.e. heterologous or foreign) sequence, such as a polypeptide or protein domain.

A "derivative" of a polypeptide or a fragment thereof may include a polypeptide modified by varying the amino acid sequence of the protein, e.g. by manipulation of the nucleic acid encoding the protein or by altering the protein itself. Such derivatives of the natural amino acid sequence may involve one or more of insertion, addition, deletion or substitution of one or more amino acids, which may be without fundamentally altering the qualitative nature of biological activity of the wild type polypeptide.

Also encompassed within the scope of the present invention are functional mimetics of active fragments of the STRAP polypeptides provided (including alleles, mutants, derivatives and variants). The term "functional mimetic" means a substance which may not contain an active portion of the relevant amino acid sequence, and probably is not a peptide at all, but which retains in qualitative terms a biological activity of natural STRAP polypeptide. The design and screening of candidate mimetics is described in detail below.

A polypeptide according to the present invention may be isolated and/or purified (e.g. using an antibody) for instance after production by expression from encoding nucleic acid (for which see below). Thus, a polypeptide may be provided free or substantially free from contaminants with which it is naturally associated (if it is a naturally-occurring polypeptide). A polypeptide may be provided free or substantially free of other polypeptides.

Polypeptides according to the present invention may be generated wholly or partly by chemical synthesis. The isolated and/or purified polypeptide may be used in formulation of a composition, which may include at least one additional component, for example a pharmaceutical composition including a pharmaceutically acceptable excipient, vehicle or carrier. A composition including a polypeptide according to the invention may be used in prophylactic and/or therapeutic treatment as discussed below.

A polypeptide, peptide, allele, mutant, derivative or variant according to the present invention may be used as an immunogen or otherwise in obtaining specific antibodies. Antibodies are useful in purification and other manipulation of polypeptides and peptides and therapeutic contexts. This is discussed further below.

A polypeptide of the invention may be labelled with a revealing label. The revealing label may be any suitable label which allows the polypeptide to be detected. Suitable labels include radioisotopes, e.g. 125I, enzymes, antibodies, polynucleotides and linkers such as biotin. Labelled polypeptides of the invention may be used in diagnostic procedures such as immunoassays in order to determine the amount of a polypeptide of the invention in a sample. Polypeptides or labelled polypeptides of the invention may also be used in serological or cell mediated immune assays for the detection of immune reactivity to said polypeptides in animals and humans using standard protocols.

A polypeptide or labelled polypeptide of the invention or fragment thereof may also be fixed to a solid phase, for example the surface of an immunoassay well or dipstick.

Such labelled and/or immobilized polypeptides may be packaged into kits in a suitable container along with suitable reagents, controls, instructions and the like.

Such polypeptides and kits may be used in methods of detection of antibodies to such polypeptides present in a sample or active portions or fragments thereof by immunoassay.

Immunoassay methods are well known in the art and will generally comprise:
(a) providing a polypeptide comprising an epitope bindable by an antibody against said protein;
(b) incubating a biological sample with said polypeptide under conditions which allow for the formation of an antibody-antigen complex; and
(c) determining whether antibody-antigen complex comprising said polypeptide is formed.

A polypeptide according to the present invention may be used in screening for molecules which affect or modulate its activity or function, e.g its interactions with p300 coactivator complex and/or its effect on p53 activity. Such molecules may interact with the N terminal region (residues 1 to 123), a region between amino acids 124 to 205 or a C terminal (residues 206 to 440) region of STRAP or with one or more regions of JMY and/or p300 which bind to STRAP, and may be useful in a therapeutic (including prophylactic) context.

It is well known that pharmaceutical research leading to the identification of a new drug may involve the screening of very large numbers of candidate substances, both before and even after a lead compound has been found. This is one factor which makes pharmaceutical research very expensive and time-consuming. Means for assisting in the screening process can have considerable commercial importance and utility. Such means for screening for substances potentially useful in modulating (i.e. activating or reducing) the activity of p53 and treating or preventing p53 induced apoptosis are provided by polypeptides according to the present invention.

Substances identified as modulators of the interactions described herein are extremely useful in the modulation of a range of stress related p53 activities since they provide basis for design and investigation of therapeutics for in vivo use. Furthermore, they may be useful in any of a number of conditions in which p53 activity is undesirable, including cancer-therapy genotoxicity, p53 dependent neuronal death in the central nervous system (i.e. brain or spinal cord injury), preservation of tissues or organs prior to transplant, preparation of host for bone marrow transplant, reducing neuronal damage during seizures, and suppression of cell aging. As noted elsewhere, STRAP and fragments thereof may also be useful in combating any of these conditions and disorders.

In various further aspects the present invention relates to screening and assay methods and means, and substances identified thereby.

The identification of the polypeptide expressed by the STRAP gene enables assays to be developed to identify further cellular proteins with which the polypeptide is associated, in addition to p300 and JMY. For example, polypeptides of the present invention may be required in a regulatory pathway in which their function is to interact with other factors which in turn promote or maintain essential cellular functions associated with cell cycle control. The polypeptides of the present invention may be used in two-hybrid assays as described below to determine cellular factors with which they become associated.

Assay methods may therefore be for substances or agents which interact with or bind a polypeptide of the invention and/or modulate one or more of its activities.

Further aspects of the present invention provide the use of a STRAP polypeptide or peptide (particularly a fragment of a polypeptide of the invention as disclosed), and/or encoding nucleic acid therefor, in screening or searching for and/or obtaining/identifying a substance, e.g. peptide or chemical compound, which interacts and/or binds with the STRAP polypeptide or peptide and/or interferes with the interaction between STRAP and JMY and/or STRAP and p300 and which is therefore a candidate modulator of the function or activity of the p300 co-factor complex. Such a substance may be useful in modulating the activity of p53, for example by means of modulating the half life of p53 and/or modulating the activity of target genes which execute the p53 stress response.

For instance, a method according to one aspect of the invention includes providing a polypeptide or peptide of the invention and bringing it into contact with a substance, which contact may result in binding between the polypeptide or peptide and the substance. Binding may be determined by any of a number of techniques available in the art, both qualitative and quantitative.

A method of screening for a substance which modulates the binding activity of a STRAP polypeptide may include contacting one or more test substances with the STRAP polypeptide in a suitable reaction medium, testing the binding activity of the treated polypeptide and comparing that activity with the binding activity of the STRAP polypeptide in comparable reaction medium untreated with the test substance or substances. A difference in binding activity between the treated and untreated polypeptides is indicative of a modulating effect of the relevant test substance or substances.

Corresponding aspects of the present invention relate to methods of screening for a substance which modulates the binding activity of a polypeptide consisting of residues 683 to 983 of JMY or a polypeptide consisting of residues 1 to 595 or 1572 to 1921 of p300.

In various aspects the present invention is concerned with provision of assays for substances which inhibit interaction between a polypeptide of the invention and one or more of JMY and p300.

One aspect of the present invention provides an assay method which includes:
 (i) bringing into contact a STRAP polypeptide according to the invention and a putative binding molecule or other test substance; and
 (ii) determining interaction or binding between the STRAP polypeptide and the test substance.

A substance which interacts with a STRAP polypeptide or peptide of the invention may be isolated and/or purified, manufactured and/or used to modulate its activity as discussed.

A further aspect of the present invention provides an assay method for screening for a substance which modulates the binding of JMY and STRAP, including:

(i) bringing a STRAP polypeptide into contact with a JMY polypeptide in the presence of one or more test substances; and
 (ii) determining the binding of the STRAP polypeptide to the JMY polypeptide.

The STRAP polypeptide may be brought into contact with the JMY polypeptide in the presence of a p300 polypeptide.

Another aspect of the present invention provides an assay method for screening for a substance which modulates the binding of p300 and STRAP, including:
 (i) bringing a STRAP polypeptide into contact with a p300 polypeptide in the presence of one or more test substances; and
 (ii) determining the binding of the STRAP polypeptide to the p300 polypeptide.

The STRAP polypeptide may be brought into contact with the p300 polypeptide in the presence of a JMY polypeptide.

Another aspect of the present invention provides an assay method for screening for a substance which modulates the binding of JMY, p300 and STRAP, including:
 (i) bringing a STRAP polypeptide into contact with a p300 polypeptide and a JMY polypeptide in the presence of one or more test substances; and
 (ii) determining the binding of the STRAP polypeptide to the p300 polypeptide and the JMY polypeptide.

An assay may be carried out under conditions in which in the absence of the test substance being an inhibitor, the STRAP polypeptide binds to the JMY or p300 polypeptide.

In assays of the present invention, the binding of a JMY and/or p300 polypeptide to a STRAP polypeptide may be determined in the presence and absence of the test substance. A difference in binding activity in the presence of test substance is indicative of a modulating effect of the relevant test substance or substances.

An assay method may comprise determining the p53 stress response in the presence and/or absence of said test substance as described herein.

As mentioned above, it is not necessary to use the entire proteins for assays of the invention which test for binding between two molecules. Fragments may be generated and used in any suitable way known to those of skill in the art. Suitable ways of generating fragments include, but are not limited to, recombinant expression of a fragment from encoding DNA. Such fragments may be generated by taking encoding DNA, identifying suitable restriction enzyme recognition sites either side of the portion to be expressed, and cutting out said portion from the DNA. The portion may then be operably linked to a suitable promoter in a standard commercially available expression system. Another recombinant approach is to amplify the relevant portion of the DNA with suitable PCR primers. Small fragments (e.g. up to about 20 or 30 amino acids) may also be generated using peptide synthesis methods which are well known in the art.

The precise format of the assay of the invention may be varied by those of skill in the art using routine skill and knowledge. For example, the interaction between the polypeptides may be studied in vitro by labelling one with a detectable label and bringing it into contact with the other which has been immobilised on a solid support. Suitable detectable labels include 35S-methionine which may be incorporated into recombinantly produced peptides and polypeptides. Recombinantly produced peptides and polypeptides may also be expressed as a fusion protein containing an epitope which can be labelled with an antibody.

Fusion proteins may be generated that incorporate six histidine residues at either the N-terminus or C-terminus of the recombinant protein. Such a histidine tag may be used for purification of the protein by using commercially available columns which contain a metal ion, either nickel or cobalt (Clontech, Palo Alto, Calif., USA). These tags also serve for detecting the protein using commercially available monoclonal antibodies directed against the six histidine residues (Clontech, Palo Alto, Calif., USA).

The protein which is immobilized on a solid support may be immobilized using an antibody against that protein bound to a solid support or via other technologies which are known per se. A preferred in vitro interaction may utilise a fusion protein including glutathione-S-transferase (GST). This may be immobilized on glutathione agarose beads. In an in vitro assay format of the type described above a test compound can be assayed by determining its ability to diminish the amount of labelled peptide or polypeptide which binds to the immobilized GST-fusion polypeptide. This may be determined by fractionating the glutathione-agarose beads by SDS-polyacrylamide gel electrophoresis. Alternatively, the beads may be rinsed to remove unbound protein and the amount of protein which has bound can be determined by counting the amount of label present in, for example, a suitable scintillation counter.

In an alternative mode, one of STRAP polypeptide and p300 or JMY polypeptide may be labelled with a fluorescent donor moiety and the other labelled with an acceptor which is capable of reducing the emission from the donor. This allows an assay according to the invention to be conducted by fluorescence resonance energy transfer (FRET). In this mode, the fluorescence signal of the donor will be altered when STRAP and p300 or JMY interact. The presence of a candidate modulator compound which modulates the interaction will increase the amount of unaltered fluorescence signal of the donor.

FRET is a technique known per se in the art and thus the precise donor and acceptor molecules and the means by which they are linked to STRAP and p300 or JMY may be accomplished by reference to the literature.

Suitable fluorescent donor moieties are those capable of transferring fluorogenic energy to another fluorogenic molecule or part of a compound and include, but are not limited to, coumarins and related dyes such as fluoresceins, rhodols and rhodamines, resorufins, cyanine dyes, bimanes, acridines, isoindoles, dansyl dyes, aminophthalic hydrazines such as luminol and isoluminol derivatives, aminophthalimides, aminonaphthalimides, aminobenzofurans, aminoquinolines, dicyanohydroquinones, and europium and terbium complexes and related compounds.

Suitable acceptors include, but are not limited to, coumarins and related fluorophores, xanthenes such as fluoresceins, rhodols and rhodamines, resorufins, cyanines, difluoroboradiazaindacenes, and phthalocyanines.

A preferred donor is fluorescein and preferred acceptors include rhodamine and carbocyanine. The isothiocyanate derivatives of these fluorescein and rhodamine, available from Aldrich Chemical Company Ltd, Gillingham, Dorset, UK, may be used to label STRAP or JMY or p300/CBP. For attachment of carbocyanine, see for example Guo et al, J. Biol. Chem., 270; 27562-8, 1995.

Another assay format is dissociation enhanced lanthanide fluorescent immunoassay (DELFIA) (Ogata et al, 1992). This is a solid phase based system for measuring the interaction of two macromolecules. Typically one molecule (either STRAP or JMY or p300) is immobilised to the surface of a multi well plate and the other molecule is added in solution to this. Detection of the bound partner is achieved by using a label consisting of a chelate of a rare earth metal. This label can be directly attached to the interacting molecule or may be introduced to the complex via an antibody to the molecule or to the molecules epitope tag. Alternatively, the molecule may be attached to biotin and a streptavidin-rare earth chelate used as the label. The rare earth used in the label may be europium, samarium, terbium or dysprosium. After washing to remove unbound label, a detergent containing low pH buffer is added to dissociate the rare earth metal from the chelate. The highly fluorescent metal ions are then quantitated by time resolved fluorimetry. A number of labelled reagents are commercially available for this technique, including streptavidin, antibodies against glutathione-S-transferase and against hexahistidine.

An assay according to the present invention may also take the form of an in vivo assay. The in vivo assay may be performed in a cell line such as a yeast strain in which the relevant polypeptides or peptides are expressed from one or more vectors introduced into the cell.

In vivo assays may also take the form of two-hybrid assays wherein STRAP and p300 or JMY are expressed as fusion proteins, one being a fusion protein comprising a DNA binding domain (DBD), such as the yeast GAL4 binding domain, and the other being a fusion protein comprising an activation domain, such as that from GAL4 or VP16. In such a case the host cell (which again may be bacterial, yeast, insect or mammalian, particularly yeast or mammalian) will carry a reporter gene construct with a promoter comprising a DNA binding elements compatible with the DBD.

STRAP and JMY or p300 and the reporter gene, may be introduced into the cell and expressed transiently or stably.

Alternatively, assays of the invention may be conducted by utilizing the ability of a STRAP-p300 complex (including JMY) to mediate the activation of a reporter gene or to induce a cellular response in a cell, particularly apoptosis. For example, a number of transcription factors, including the glucocorticoid receptor (GR) and E2F-1, are known to be regulated by p300/CBP, as is p53. We have found that the regulation of such factors is enhanced by STRAP. Further, we have found that p53-mediated apoptosis is enhanced by the presence of STRAP.

Thus assays of the invention include an assay for a modulator of STRAP-p300 complex formation which comprises:

a) providing STRAP, p300 and JMY together with a regulatory factor which is a target for p300, in the presence of a putative modulator and a reporter gene which comprises a target promoter for said regulatory factor; and b) measuring the modulation of transcription of the reporter gene caused by the presence of said modulator.

The regulatory factor includes GR for which suitable promoters include promoters which contain a GRE such as c-myc and the MMLV LTR; E2F-1 for which suitable promoters include cyclin A, cyclin E, tyrosine amino transferase and the E2F-1 gene promoter; p53 for which suitable promoters include Bax, Waf1/Cip, Gadd45 and cyclin G; oestrogen receptor (ER) for which suitable promoters include progesterone receptor and PS-2; and other nuclear receptors and promoters containing recognition elements of this type. Suitable reporter genes operably linked to the promoter include chloramphenicol acetyl transferase, luciferase, green fluorescent protein and β-galactosidase. In the case of ER, a the 13 base palindromic estrogen response element (ERE) may be included in the promoter of a reporter construct to provide a suitable reporter gene. In an alternative embodiment, the assay may be conducted in a cell lacking wild-type p53 and which undergoes apoptosis in the presence of p53. Such cells include SAOS-2 cells.

In this format the assay will be conducted by supplying to the cell expression vector(s) encoding STRAP, JMY, p300/CBP and wild type p53, treating said cells with a putative modulator and measuring the effect of the modulator on apoptosis of the cells. Apoptosis may also be measured in an analogous manner in cell lines with wild type p53 wherein apoptosis is enhanced by the presence of, for example, excess STRAP.

Assays will be run with suitable controls routine to those of skill in the art.

Accordingly, another aspect of the present invention is a substance obtainable using an assay method as described herein.

Such a substance may include polypeptide, antibody, peptide, nucleic acid molecule, small molecule or other pharmaceutically useful compound. In some embodiments of this aspect of the invention, a polypeptide has less than 900 residues and/or does not include the full length JMY and p300 sequences.

Combinatorial library technology (Schultz, J S (1996) Biotechnol. Prog. 12:729-743) provides an efficient way of testing a potentially vast number of different substances for ability to modulate activity of a polypeptide. Prior to, or as well as, being screened for modulation of activity, test substances may be screened for ability to interact with the polypeptide, e.g. in a yeast two-hybrid system (which requires that both the polypeptide and the test substance can be expressed in yeast from encoding nucleic acid). This may be used as a coarse screen prior to testing a substance for actual ability to modulate activity of the polypeptide.

The amount of test substance or compound which may be added to an assay of the invention will normally be determined by trial and error depending upon the type of compound used. Typically, from about 0.01 to 100 µM concentrations of putative inhibitor compound may be used, for example from 0.1 to 10 µM. Greater concentrations may be used when a peptide is the test substance.

Compounds which may be used may be natural or synthetic chemical compounds used in drug screening programmes. Extracts of plants which contain several characterised or uncharacterised components may also be used. A further class of putative inhibitor compounds can be derived from the STRAP polypeptide or the JMY polypeptide and/or p300 polypeptide which to which it binds. Peptide fragments of from 5 to 40 amino acids, for example from 6 to 10 amino acids from the region of the relevant polypeptide responsible for interaction, may be tested for their ability to disrupt such interaction.

Other candidate inhibitor compounds may be based on modelling the 3-dimensional structure of a polypeptide or peptide fragment and using rational drug design to provide potential inhibitor compounds with particular molecular shape, size and charge characteristics.

Following identification of a substance which modulates or affects polypeptide activity, the substance may be investigated further. Furthermore, it may be manufactured and/or used in preparation, i.e. manufacture or formulation, of a composition such as a medicament, pharmaceutical composition or drug. These may be administered to individuals.

Thus, the present invention extends in various aspects not only to a substance identified as a modulator of polypeptide activity, in accordance with what is disclosed herein, but also a pharmaceutical composition, medicament, drug or other composition comprising such a substance, a method comprising administration of such a composition to a patient, e.g. for treatment (which may include preventative treatment) of a condition related to stress induced p53 dependent cell apoptosis, such as DNA damage (for example caused by UV radiation), cancer-therapy genotoxicity (for example, caused by chemo- or radiation therapy), p53 dependent neuronal death in the central nervous system (i.e. brain or spinal cord injury), preservation of tissues or organs prior to transplant, preparation of host for bone marrow transplant, reducing neuronal damage during seizures and suppression of cell aging, use of such a substance in manufacture of a composition for administration, e.g. for treatment of a condition related to p53 dependent cell apoptosis (such as hyperthermia, hypoxia, stroke, ischemia, acute inflammation, burn or cell aging), and a method of making a pharmaceutical composition comprising admixing such a substance with a pharmaceutically acceptable excipient, vehicle or carrier, and optionally other ingredients.

Cancer therapy includes radio- and chemo-therapy.

A substance identified using as a modulator of polypeptide or promoter function may be peptide or non-peptide in nature. Non-peptide "small molecules" are often preferred for many in vivo pharmaceutical uses. Accordingly, a mimetic or mimic of the substance (particularly if a peptide) may be designed for pharmaceutical use. The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, e.g. peptides are not well suited as active agents for oral compositions as they tend to be quickly degraded by proteases in the alimentary canal. Mimetic design, synthesis and testing may be used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been found, its structure is modelled to according its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in vivo or clinical testing.

Mimetics of substances identified as having ability to modulate STRAP polypeptide activity using a screening method as disclosed herein are included within the scope of the present invention. A polypeptide, peptide or substance able to modulate activity of a STRAP polypeptide according to the present invention may be provided in a kit, e.g. sealed in a suitable container which protects its contents from the external environment. Such a kit may include instructions for use.

A convenient way of producing a polypeptide according to the present invention is to express nucleic acid encoding it, by use of the nucleic acid in an expression system. Accordingly, the present invention also encompasses a method of making a polypeptide (as disclosed), the method including expression from nucleic acid encoding the polypeptide (generally nucleic acid according to the invention). This may conveniently be achieved by growing a host cell in culture, containing such a vector, under appropriate conditions which cause or allow expression of the polypeptide. Polypeptides may also be expressed in in vitro systems, such as reticulocyte lysate.

Systems for cloning and expression of a polypeptide in a variety of different host cells are well known. Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others. A common, preferred bacterial host is *E. coli*. Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1992.

Thus, a further aspect of the present invention provides a host cell containing nucleic acid as disclosed herein. The nucleic acid of the invention may be integrated into the genome (e.g. chromosome) of the host cell. Integration may be promoted by inclusion of sequences which promote recombination with the genome, in accordance with standard techniques. The nucleic acid may be on an extra-chromosomal vector within the cell.

A still further aspect provides a method which includes introducing the nucleic acid into a host cell. The introduction, which may (particularly for in vitro introduction) be generally referred to without limitation as "transformation", may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage.

Marker genes such as antibiotic resistance or sensitivity genes may be used in identifying clones containing nucleic acid of interest, as is well known in the art.

The introduction may be followed by causing or allowing expression from the nucleic acid, e.g. by culturing host cells (which may include cells actually transformed although more likely the cells will be descendants of the transformed cells) under conditions for expression of the gene, so that the encoded polypeptide is produced. If the polypeptide is expressed coupled to an appropriate signal leader peptide it may be secreted from the cell into the culture medium. Following production by expression, a polypeptide may be isolated and/or purified from the host cell and/or culture medium, as the case may be, and subsequently used as desired, e.g. in the formulation of a composition which may include one or more additional components, such as a pharmaceutical composition which includes one or more pharmaceutically acceptable excipients, vehicles or carriers (e.g. see below).

Introduction of nucleic acid may take place in vivo by way of gene therapy, as discussed below. A host cell containing nucleic acid according to the present invention, e.g. as a result of introduction of the nucleic acid into the cell or into an ancestor of the cell and/or genetic alteration of the sequence endogenous to the cell or ancestor (which introduction or alteration may take place in vivo or ex vivo), may be comprised (e.g. in the soma) within an organism which is an animal, particularly a mammal, which may be human or non-human, such as rabbit, guinea pig, rat, mouse or other rodent, cat, dog, pig, sheep, goat, cattle or horse, or which is a bird, such as a chicken. Genetically modified or transgenic animals or birds comprising such a cell are also provided as further aspects of the present invention.

In another aspect of the invention, there is provided a method for producing a transgenic non-human mammal, particularly a rodent such as a mouse, by incorporating a lesion into the locus of a STRAP gene.

This may be achieved in a variety of ways. A typical strategy is to use targeted homologous recombination to replace, modify or delete the wild-type STRAP gene in an embryonic stem (ES) cell. An targeting vector is introduced into ES cells by electroporation, lipofection or microinjection. In a few ES cells, the targeting vector pairs with the cognate chromosomal DNA sequence and transfers the desired mutation carried by the vector into the genome by homologous recombination. Screening or enrichment procedures are used to identify the transfected cells, and a transfected cell is cloned and maintained as a pure population. Next, the altered ES cells are injected into the blastocyst of a preimplantation mouse embryo or alternatively an aggregation chimera is prepared in which the ES cells are placed between two blastocysts which, with the ES cells, merge to form a single chimeric blastocyst. The chimeric blastocyst is surgically transferred into the uterus of a foster mother where the development is allowed to progress to term. The resulting animal will be a chimera of normal and donor cells. Typically the donor cells will be from an animal with a clearly distinguishable phenotype such as skin colour, so that the chimeric progeny is easily identified. The progeny is then bred and its descendants cross-bred, giving rise to heterozygotes and homozygotes for the targeted mutation. The production of transgenic animals is described further by Capecchi, M, R., 1989, Science 244; 1288-1292; Valancius and Smithies, 1991, Mol. Cell. Biol. 11; 1402-1408; and Hasty et al, 1991, Nature 350; 243-246, the disclosures of which are incorporated herein by reference.

Homologous recombination in gene targeting may be used to replace the wild-type STRAP gene with a specifically defined mutant form (e.g truncated or containing one or more substitutions).

The invention may also be used to replace the wild-type gene with a modified gene capable of expressing a wild-type or otherwise active STRAP polypeptide, where the expression may be selectively blocked either permanently or temporarily. Permanent blocking may be achieved by supplying means to delete the gene in response to a signal. An example of such a means is the cre-lox system where phage lox sites are provided at either end of the transgene, or at least between a sufficient portion thereof (e.g. in two exons located either side or one or more introns). Expression of a cre recombinase causes excision and circularisation of the nuclei acid between the two lox sites. Various lines of transgenic animals, particularly mice, are currently available in the art which express cre recombinase in a developmentally or tissue restricted manner, see for example Tsien, Cell, Vol.87(7): 1317-1326, (1996) and Betz, Current Biology, Vol.6(10): 1307-1316 (1996). These animals may be crossed with lox transgenic animals of the invention to examine the function of the STRAP gene. An alternative mechanism of control is to supply a promoter from a tetracyline resistance gene, tet, to the control regions of the STRAP locus such that addition of tetracyline to a cell binds to the promoter and blocks expression of the STRAP gene.

Transgenic targeting techniques may also be used to delete the STRAP gene. Methods of targeted gene deletion are described by Brenner et al, WO94/21787 (Cell Genesys), the disclosure of which is incorporated herein by reference.

Homologous recombination may also be used to produce "knock in" animals which express a polypeptide of the invention in the form of a fusion protein, fused to a detectable tag such as β-galactosidase or green fluorescent protein. Such transgenic non-human mammals may be used in methods of determining temporal and spatial expression of the STRAP gene by monitoring the expression of the detectable tag.

A further alternative is to target control sequences responsible for expression of the STRAP gene.

The invention extends to transgenic non-human mammals obtainable by such methods and to their progeny. Such mammals may be homozygous or heterozygous. Such mammals include mice, rodents, rabbits, sheep, goats, pigs.

Transgenic non-human mammals may be used for experimental purposes in studying the role of STRAP in regulating the cell cycle and in the development of therapies designed to target the interaction of STRAP with other cellular factors, particularly p300 and JMY. By "experimental" it is meant permissible for use in animal experimentation or testing purposes under prevailing legislation applicable to the research facility where such experimentation occurs.

Instead of or as well as being used for the production of a polypeptide encoded by a transgene, host cells may be used as a nucleic acid factory to replicate the nucleic acid of interest in order to generate large amounts of it. Multiple copies of nucleic acid of interest may be made within a cell when coupled to an amplifiable gene such as dihydrofolate reductase (DHFR), as is well known. Host cells transformed with nucleic acid of interest, or which are descended from host cells into which nucleic acid was introduced, may be cultured under suitable conditions, e.g. in a fermentor, taken from the culture and subjected to processing to purify the nucleic acid. Following purification, the nucleic acid or one or more fragments thereof may be used as desired.

The provision of the novel STRAP polypeptide also enables, for the first time, the production of antibodies able to bind specifically to this molecule.

Accordingly, a further aspect of the present invention provides an antibody able to bind specifically to the polypeptide whose sequence is given in a figure herein. Such an antibody may be specific in the sense of being able to distinguish between the polypeptide it is able to bind and other human polypeptides for which it has no or substantially no binding affinity (e.g. a binding affinity of about 1000× less). Specific antibodies bind an epitope on the molecule which is either not present or is not accessible on other molecules. Antibodies according to the present invention may be specific for the wild-type polypeptide. Antibodies according to the invention may be specific for a particular mutant, variant, allele or derivative polypeptide as between that molecule and the wild-type polypeptide, so as to be useful in diagnostic and prognostic methods as discussed below. Antibodies are also useful in purifying the polypeptide or polypeptides to which they bind, e.g. following production by recombinant expression from encoding nucleic acid.

Preferred antibodies according to the invention are isolated, in the sense of being free from contaminants such as antibodies able to bind other polypeptides and/or free of serum components. Monoclonal antibodies are preferred for some purposes, though polyclonal antibodies are within the scope of the present invention.

The invention further provides immunological assays which comprise:
 (a) bringing a body sample from said subject into contact, under binding conditions, with an antibody of the invention; and
 (b) determining whether said antibody has been able to bind to a polypeptide in said sample.

Antibodies may be obtained using techniques which are standard in the art. Methods of producing antibodies include immunising a mammal (e.g., mouse, rat, rabbit, horse, goat, sheep or monkey) with the protein or a fragment thereof. Antibodies may be obtained from immunised animals using any of a variety of techniques known in the art, and screened, preferably using binding of antibody to antigen of interest. For instance, Western blotting techniques or immunoprecipitation may be used (Armitage et al., 1992, Nature 357: 80-82). Isolation of antibodies and/or antibody-producing cells from an animal may be accompanied by a step of sacrificing the animal.

As an alternative or supplement to immunising a mammal with a peptide, an antibody specific for a protein may be obtained from a recombinantly produced library of expressed immunoglobulin variable domains, e.g. using lambda bacteriophage or filamentous bacteriophage which display functional immunoglobulin binding domains on their surfaces; for instance see WO92/01047.

Suitable peptides for use in immunising an animal and/or isolating anti-STRAP antibody include peptides which have the residues 36-46 of FIG. 1 (SEQ ID NO:1 or SEQ ID NO:2).

Antibodies according to the present invention may be modified in a number of ways. Indeed, the term "antibody" should be construed as covering antibody fragments such as Fab and scFv fragments, derivatives, functional equivalents and homologues of antibodies, including synthetic molecules and molecules whose shape mimicks that of an antibody enabling it to bind an antigen or epitope.

The reactivities of antibodies on a sample may be determined by any appropriate means. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule.

One favoured mode is by covalent linkage of each antibody with an individual fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

Antibodies according to the present invention may be used in screening for the presence of a polypeptide, for example in a test sample containing cells or cell lysate as discussed, and may be used in purifying and/or isolating a polypeptide according to the present invention, for instance following production of the polypeptide by expression from encoding nucleic acid therefor. Antibodies may modulate the activity of the polypeptide to which they bind and so may be useful in a therapeutic context (which may include prophylaxis) to modulate the p53 dependent response to cellular stress.

The present invention also provides a substance as described herein for use in a pharmaceutical composition for the modulation of the p53 dependent cell stress response in an individual. Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors.

A composition may be administered alone or in combination with other treatments, either simultaneously or sequentially dependent upon the condition to be treated.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, or Lactated Ringer's Injection. Preservatives, stabilisers, buffers, antioxidants and/or other additives may be included, as required.

Targeting therapies may be used to deliver the active agent more specifically to certain types of cell, by the use of targeting systems such as antibody or cell specific ligands. Targeting may be desirable for a variety of reasons; for example if the agent is unacceptably toxic, or if it would otherwise require too high a dosage, or if it would not otherwise be able to enter the target cells.

Instead of administering an agent directly, it may be produced in target cells by expression from an encoding gene introduced into the cells, e.g. in a viral vector (see below). The vector may be targeted to the specific cells to be treated, or it may contain regulatory elements which are switched on more or less selectively by the target cells. Viral vectors may be targeted using specific binding molecules, such as a sugar, glycolipid or protein such as an antibody or binding fragment thereof. Nucleic acid may be targeted by means of linkage to a protein ligand (such as an antibody or binding fragment thereof) via polylysine, with the ligand being specific for a receptor present on the surface of the target cells.

An agent may be administered in a precursor form, for conversion to an active form by an activating agent produced in, or targeted to, the cells to be treated.

Pharmaceutical compositions as described herein may be used for anti-sense regulation of gene expression, e.g. targeting an antisense nucleic acid molecule to cells in which a mutant form of the gene is expressed, the aim being to reduce production of the mutant gene product. Other approaches to specific down-regulation of genes are well known, including the use of ribozymes designed to cleave specific nucleic acid sequences. Ribozymes are nucleic acid molecules, actually RNA, which specifically cleave single-stranded RNA, such as mRNA, at defined sequences, and their specificity can be engineered. Hammerhead ribozymes may be preferred because they recognise base sequences of about 11-18 bases in length, and so have greater specificity than ribozymes of the Tetrahymena type which recognise sequences of about 4 bases in length, though the latter type of ribozymes are useful in certain circumstances. References on the use of ribozymes include Marschall, et al. Cellular and Molecular Neurobiology, 1994. 14(5): 523; Hasselhoff, Nature 334: 585 (1988) and Cech, J. Amer. Med. Assn., 260: 3030 (1988).

Aspects of the present invention will now be illustrated with reference to the accompanying figures described below by experimental exemplification, by way of example and not limitation. Further aspects and embodiments will be appar- Experimental Materials and Methods Plasmids The following plasmids were used; pCMV-p300, pCMV-JMY, pVP16-JMY, pG4-p300, pET-JMY, pCMV-HA-JMY469-558, pCMV-HA-JMY1-403, PCMV-HA-JMY119-403, pET-JMY1-504, pCMV-HA-JMY502-983, pCMV-HA-JMY1-119, pCMV-HA-JMY468-558, pCMV-HA-JMY683-983 and pCMV-HA-NAP2 were as described (Shikama et al., 2000; submitted). Flag-tagged p300, pGEXT-2T-p300744-1571, pGEXT-2T-p3001572-2370, pCMV-p300619-1303, pCMV-p3001257-2284, pCMV-p3001257-19 21, pCMV-p53, pCMV-p5322/23, (Lin et al., 1994), pBax-luc (Miyashita and Reed, 1995), pWWP-luc (El-Deiry et al., 1993), pCMV-β-gal (Zamanian and La Thangue, 1992), pG5-luc and pTG13 (Lee et al., 1998) and pCMV-HDM2 (Loughran and La Thangue, 2000).

For the preparation of the STRAP expression vectors, pG4-STRAP8-438 was made by subcloning the appropriate region of the STRAP cDNA into EcoRI/NotI sites. pVP16-STRAP8-123 was made by subcloning into BamHI/XhoI site. pETSTRAP8-438 and pETSTRAP8-123 were constructed by subcloning into pET28A and pET28C respectively, digested with BamHI/XhoI. pCMV-HA-STRAP8-438, pCMV-HA-STRAP8-205, pCMV-HA-STRAP123-205, pCMV-HA-STRAP206-438, pCMV-HA-STRAP206-327 and pCMV-HA-STRAP328-438 were created by subcloning the appropriate cDNA fragment into the BamHI/XhoI site or for pCMV-HA-STRAP8-123 into the XhoI/XbaI site of pCMV-HA vector.

Antisera.

The following antisera were used; the p53 monoclonal antibody DO-1 (Santa Cruz), anti-HA monoclonal antibody Y-11 (Boehringer Mannheim), anti-p300 monoclonal antibody Ab-1 (Calbiochem), anti-p300 rabbit polyclonal C20 (Santa Cruz), anti-p300 rabbit polyclonal N-15 (Santa Cruz) and anti-JMY rabbit polyclonal antibody 789 (Shikama et al., 1999). The STRAP rabbit anti-peptide antisera, 15, was prepared by standard procedures against a STRAP peptide representing from residue 30 to 46.

Isolation of STRAP.

The yeast strain CTY10.5 containing the LexAβ-galactosidase reporter vector pLex (His) was as previously described (Buck et al., 1995). pLex-JMY was made by inserting into the EcORI site in frame the fragment of JMY corresponding to amino acids 469-558 with the DNA binding domain of LexA. Screening a 10.5 day mouse embryo random primed cDNA library fused to the VP16 transactivation domain (Vojtek et al., 1993) yielded a single positive clone containing 341 bp of the STRAP cDNA sequence.

Full-length STRAP cDNAs were isolated through the combined approach of screening cDNA libraries prepared from PCC4 mouse teratocarcinoma cells (Stratagene) and RACE (Clontech) using a testis cDNA library.

Transient Transfections and Reporter Assays.

For transfection into SAOS2 or U2OS cells, cells were incubated in DMEM containing 10% serum throughout and transfected with pBax-luc (Miyashita and Reed, 1995), pWWP-luc (El-Deiry et al., 1993), or pTG13 (Lee et al., 1998) expression vector for p53 (pCMV-p53), together with the indicated amounts of the STRAP expression vector and harvested 34-36 h post-transfection (Sørensen et al., 1996; Shikama et al., 1999). All transfections were performed using the calcium phosphate procedure and included the internal control pCMV-β-gal (Zamanian and La Thangue, 1992). The mammalian two-hybrid assay was performed in U2OS cells as described using the Gal4-responsive reporter pG5-luc and pG4-p300611-2283 (Lee et al., 1998) together with pVP16-STRAP, or pG4-STRAP hybrid together with pVP16-JMY.

Immunoprecipitation and Immunoblotting.

For immunoprecipitation, p53−/− MEFs, U2OS and SAOS2 cells were transfected with the expression vectors pCMV-p300 and pCMV-JMY and pCMV-HA-STRAP. After 48 h, cells were harvested in TNN buffer (50 mM Tris-HCl (pH7.4), 5 mM EDTA, 0.5% NP40, 50 mM NaF, 1 mM DTT, 0.2 mM sodium orthovanadate) and protease inhibitor cocktail (1 mM PMSF, leupeptin, aprotinin and pepstatin (1 μg/ml)) containing 120 mM NaCl and incubated on ice for 30 min.

The cell extract was first precleared for 1 h with protein G and then immunoprecipitated with the anti-HA monoclonal antibody Y11, which was collected with protein-A agarose. The agarose beads were collected and washed three times in the extraction buffer before denaturation and SDS-PAGE. Immunoblotting was subsequently performed with either an anti-p300 monoclonal antibody Ab-1 or anti-JMY polyclonal antibody.

For p53 stability studies p53−/− MEF, were transfected as described with pCMV-p53, pCMV-HDM2 and the indicated amounts of pCMV-HA-STRAP. 6 h after transfection the cells were harvested as described and submitted to SDS-PAGE and immunoblot. In the case of U2OS cells, endogenous p53 protein was followed after the transfection of pCMV-HA-STRAP. Cells were harvested and the cell extracts prepared as described above. The p53 protein was detected by immunoblotting with DO-1.

Biochemical Binding Assay.

Flag-tagged full-length p300 protein was expressed in the baculovirus expression system and bound to M2-anti-flag antibody agarose (Kodak). For the control beads, the M2-anti-flag antibody agarose was treated with cell extract from uninfected Sf9 cells.

The various JMY and STRAP proteins were in vitro translated by using TNT-coupled reticulocyte lysate system (Promega) in the presence of [35S]Met/Cys (Amersham). Each translation reaction (25 μl) was incubated either with the beads coupled to the flag-tagged p300 or the control beads for 2 h at 4° C. The protein complex on the beads was washed three times in TNN buffer containing 100 mM NaCl and eluted in 2×SDS sample buffer and loaded on to an SDS-PAGE gel. The proteins were detected by autoradiography.

For JMY469-558, in vitro translation was carried out in the absence of radioactive amino acids. The protein was detected by immunoblotting using anti-HA Y11 monoclonal antibody. Wild-type STRAP in pET28a (Novagen) was expressed and purified through His-tag chromatography according to the manufacturer's instructions (Pharmacia).

The eluted fraction containing His-STRAP was dialysed against 50 mM Tris (pH 7.5), 100 mM KCl, 20% glycerol, 0.2 mM DTT, 0.2 mM PMSF. For the in vitro binding assay, flag-tagged full-length p300 was expressed in the baculovirus system and bound to M2-anti-flag antibody agarose (Kodak). For control beads, the M2-anti-flag antibody agarose was treated with cell extract from uninfected Sf9 cells.

Wild-type JMY and STRAP in pET28a vector (Novagen) were expressed in bacteria and purified through nickel chromatography according to the manufacturer's instructions (Pharmacia). The eluted fraction containing His-STRAP and His-JMY protein was dialysed against 50 mM Tris (pH 7.5), 100 mM KCl, 20% glycerol, 0.2 mM DTT, 0.2 mM PMSF.

The binding assay using flag-p300 was performed for 3 h at 4° C. in a buffer containing Tris-pH 7.5, 250 mM NaCl, 0.1% NP40, 10% glycerol, 1.5 mM $MgCl_2$, 0.2 mM EDTA, 0.5 mg/ml BSA, 0.5 mM DTT, 0.5 mM PMSF and protease inhibitors. After binding, the beads were washed three times in 50 mM Tris-pH 7.5, 250 mM NaCl, 0.1% NP40, 10% glycerol, 1.5 mM MgCl2, 0.2 mM EDTA, 0.1 mM DTT, 0.1 mM PMSF and protease inhibitors. The level of JMY bound to p300 was detected by immunoblotting with the anti-JMY antiserum.

Cyclohexamide Treatment.

U2OS cells were transfected with the pCMV-HA-STRAP, pCMV-HA-JMY, pCMV-p300 and for control empty pcDNA3 expression vectors. After 48 h of transfection, cyclohexamide (10 µg/ml) was added to the cells for the indicated time periods and cells were harvested in TNN buffer (Maki and Howley, 1997). The cell extract was loaded on SDS-PAGE and the p53 protein was detected on nitrocellulose membrane with anti-p53 monoclonal antibody DO1.

Etoposide Treatment

Cells were transfected with the pCMV-HA-STRAP, pCMV-JMY or pCMV-p53 and for the control empty pcDNA3 expression vector. Etoposide at a final concentration of 200 nM and 400 nM was added to the cells 12 h before harvesting. Cells were harvested in TNN buffer and submitted to either immunoblotting or luciferase activity assays.

Flow Cytometry.

SAOS2 cells were transfected with pCMV-p53 or pCMV-p5322/23 (5 □g) either alone or together with pCMV-STPAP. Flow cytometry was performed as described previously (de la Luna et al. 1999; Shikama et al., 1999).

Irradiation.

Two hours after irradiation (10GyIR and 80J/m2 UV) A31, p53–/– and p53–/–/MDM2–/– MEFs, were washed twice with ice cold PBS (pH7.4). Lysis was performed on ice for 20 min in lysis buffer TNN (Tris HCl pH7.5, 50 mM, NaCl 120 mM, EDTA 1 mM, 0.5% Nonidet P-40, 1 mM PMSF, protease inhibitors). Lysates were centrifuged for 20 min, 12,000 rpm, at 4° C. and equal amounts of protein were loaded onto an SDS gel and the amount of STRAP1 determined after immunoblotting with the anti-STRAP antibody.

Results

Isolation and Characterization of STRAP.

A yeast two-hybrid assay was used to screen for proteins that are capable of physically interacting with the JMY co-factor, which is known to form a complex with p300 (Shikama et al., 1999). For the bait, we used a hybrid protein in which an internal domain of JMY from residue 469 to 558, containing a region previously assigned to the interaction with p300 (Shikama et al., 1999), was fused to the LexA DNA binding domain.

Screening of a 10.5 d.p.c. mouse embryo activation domain-tagged library identified a partial cDNA clone of novel sequence. Subsequent isolation and sequence analysis of the full-length cDNA indicated that it encoded a protein of 440 residues which lacks significant homology to any other known protein or nucleotide sequence on the currently available data bases (FIG. 1). Because of the properties of this new protein in performing a key role in facilitating stress-responsive protein-protein interactions within the p300 co-activator complex, the protein has been designated STRAP, to reflect its function as a stress-responsive activator of p300.

Figure 5:
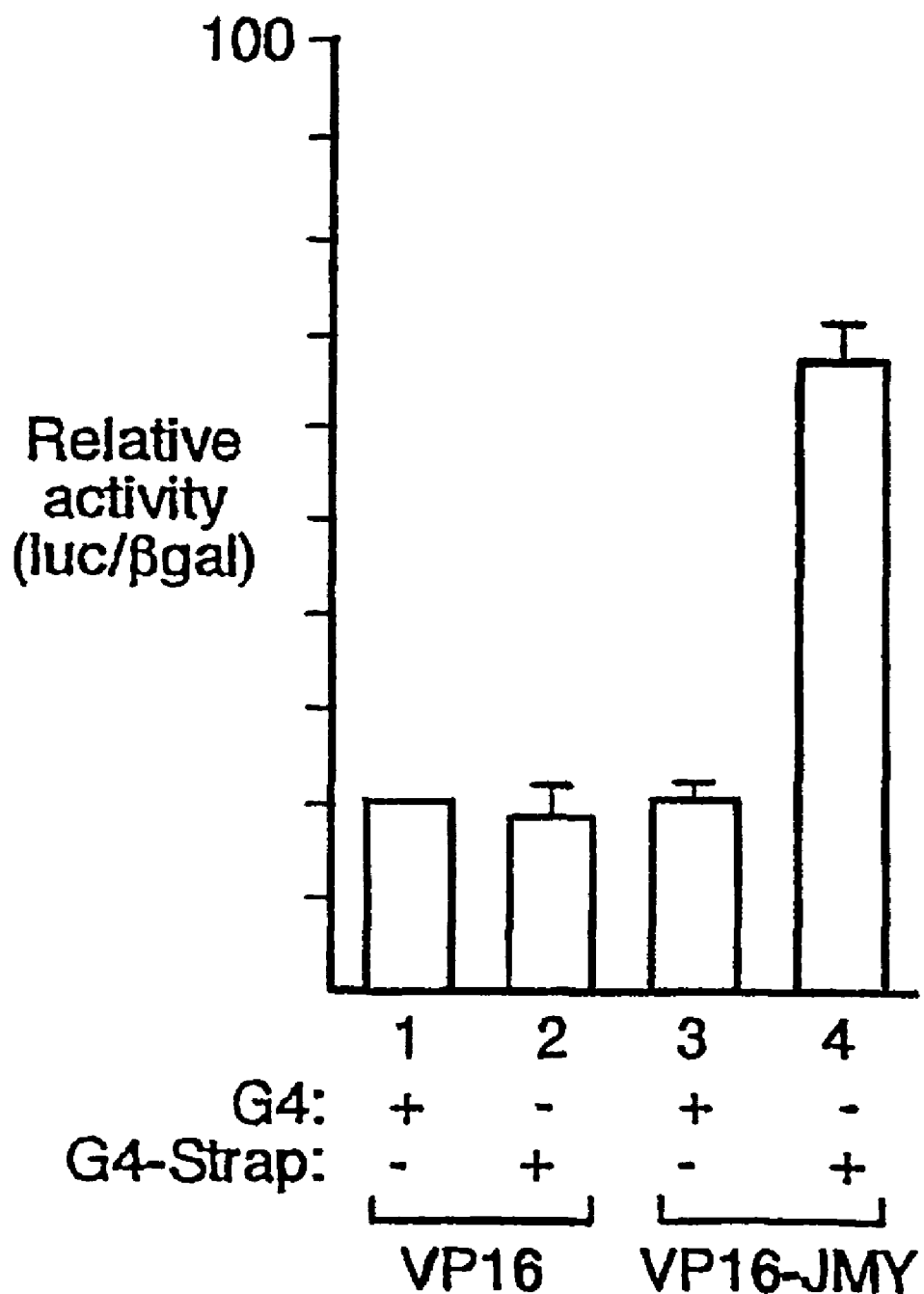
FIG. 5 shows the results of a two-hybrid assay in mammalian cells: the indicated expression vectors, either pVP16-JMY (0.5 µg) or pG4-Strap together with the control (0.5 µg), pVP16 (0.5 µg) or G4 (0.1 µg) vectors were introduced into U2OS cells as indicated, together with the reporter pG5-luc (0.5 μg) and internal control pCMV-β-gal (1 μg). The data represent the relative activity of luciferase to β-galactosidase and are the average values derived from two or more independent experiments.

A remarkable feature of STRAP is the presence of six tetratricopeptide repeat (TPR) motifs that are distributed throughout the entire length of the protein (FIGS. 4 and 5). Whilst a variety of other proteins have been found to possess TPR motifs (Lamb et al., 1995; Blatch and Lassle, 1999), STRAP appears to be quite unusual in its tandem distribution of TPR motifs. Based on multiple sequence alignments, there appear to be no strictly conserved residues in the 34 amino acid residue TPR motif (Blatch and Lassle, 1999). There are however, strong preferences for small hydrophobic residues at certain positions. The TPR motifs in STRAP fit in well with the existing information on the composition of TPR motifs.

An analysis of the pattern of expression of STRAP by northern blotting with RNA prepared from different mouse tissues including heart, brain, spleen, lung, liver, kidney and testis, indicated that expression is widespread, similar results being obtained in cell lines derived from diverse origins.

STRAP Interacts with Distinct Components of the p300 Co-activator Complex.

The TPR motif is a helical motif that can function in protein-protein interactions (Lamb et al., 1995; Blatch and Lassle, 1999). Since STRAP was isolated in a yeast two-hybrid screen using a domain of JMY as the bait, we assessed if STRAP could bind to JMY in mammalian cells and thereafter studied its interaction with other components of the co-activator complex.

Figure 6:
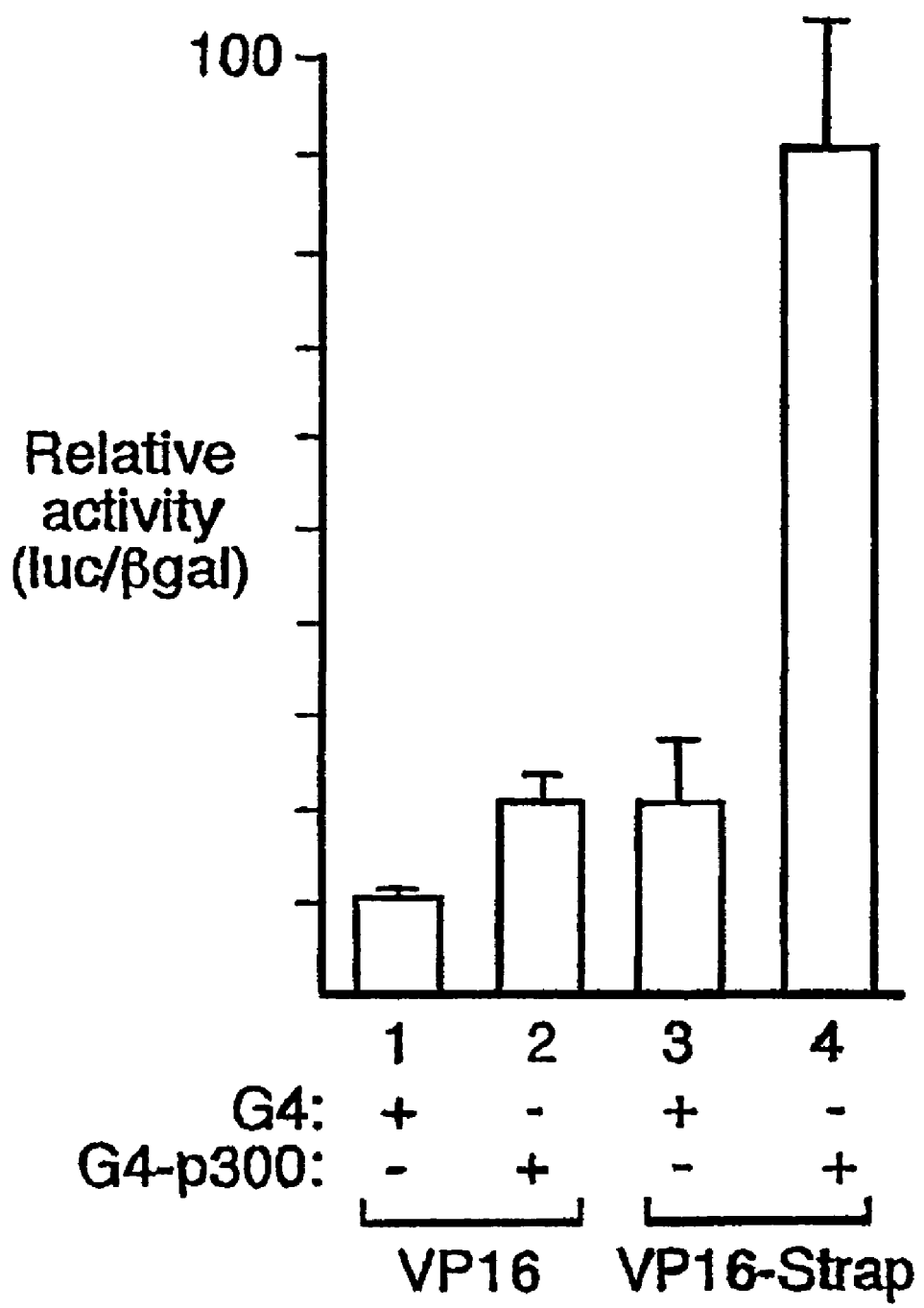
FIG. 6 shows the results of a two-hybrid assay performed in U2OS cells as described in a) using the indicated vectors, namely pVP16-Strap (0.5 μg) or pG4-p300 (0.5 μg). The data represent the average values derived from two or more independent experiments.

We performed a series of two-hybrid assays in U2OS cells, in which we found that VP16-JMY could induce the activity of a hybrid protein in which the STRAP sequence was fused to the Gal4 DNA binding domain, referred to as G4-STRAP, but not G4 alone (FIG. 5). Taking a similar approach, VP16-STRAP could induce G4-p300 (FIG. 6). These results provide indication that STRAP interacts with at least two components of the p300 co-activator complex, namely JMY and p300.

U2OS cells were transfected with expression vectors for HA-tagged STRAP together with JMY or p300, and assessed their interaction by immunoprecipitation with an anti-HA monoclonal antibody followed by immunoblotting with either anti-JMY or anti-p300. In both experiments, STRAP specifically co-immunoprecipitated with JMY and p300.

An anti-peptide antibody against STRAP was prepared to determine whether similar interactions occur under physiological conditions. This antibody reacted specifically with bacterially expressed wild-type STRAP, and recognised the exogenous STRAP polypeptide, of about 60,000 molecular weight, in transfected cells. Moreover, an endogenous polypeptide of similar molecular weight was recognised by the anti-STRAP antibody in murine A31 cells. Binding of the antibody to the 60,000 molecular weight STRAP polypeptide was blocked upon the presence of the homologous peptide. We used this anti-STRAP antibody to test whether p300 and STRAP form a complex under physiological conditions. In anti-p300 immunoprecipitates from murine A31 cells, we found STRAP to be present in the p300 immunocomplex. These results provide strong indication that STRAP and p300 exist as a complex under normal physiological conditions.

Binding Domains in STRAP, p300 and JMY.

The binding domains in STRAP for JMY and p300 were determined through a biochemical assay in which different regions of STRAP were in vitro translated and thereafter assessed for binding to either his-tagged wild-type JMY or flag-tagged wild-type p300.

Out of a panel of STRAP derivatives, two distinct regions were found to be responsible for the interaction with JMY, one located in the N-terminal region up to residue 123, and the other within residue 123 to 205; the C-terminal half of STRAP (from residue 206) exhibited little binding activity for JMY.

Figure 7:
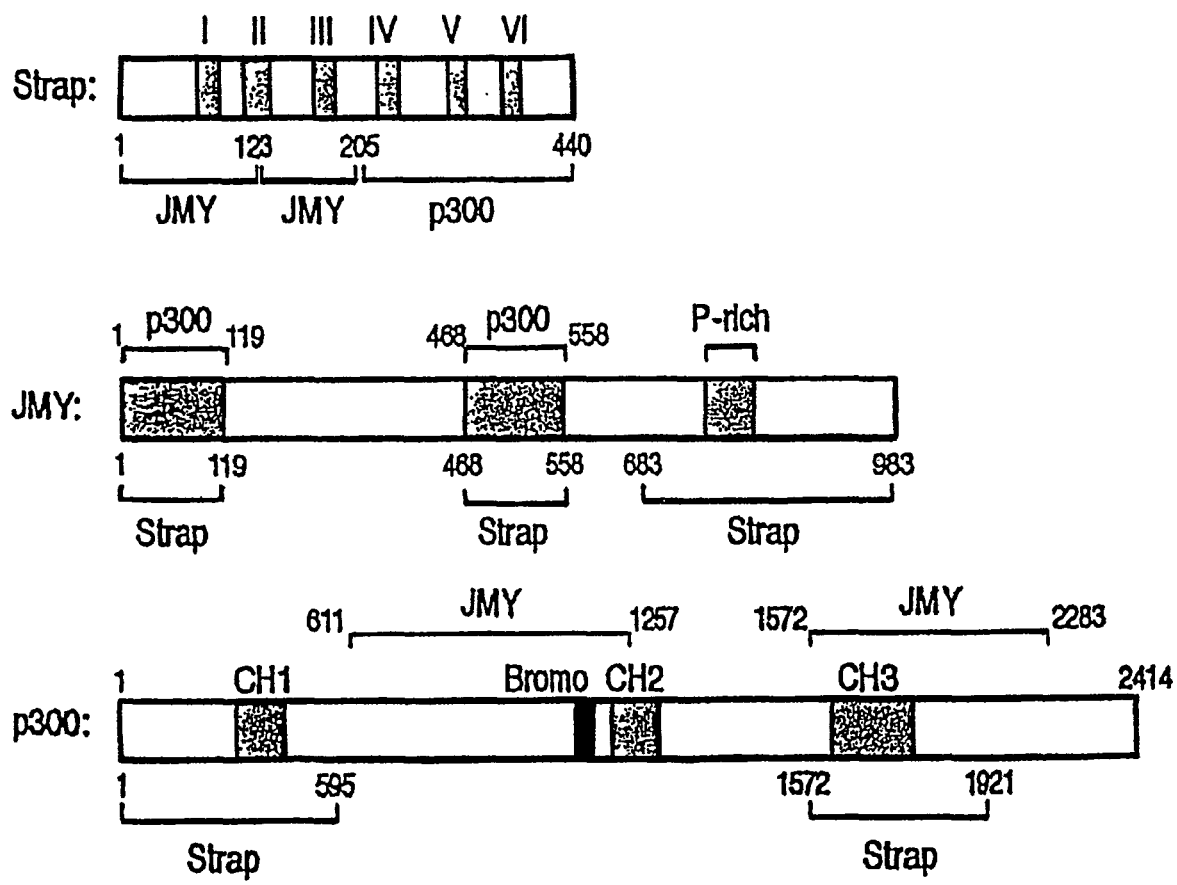
FIG. 7 shows a summary of the binding domains in Strap, JMY and p300. The binding domains in JMY for p300, and in p300 for JMY, are taken from Shikama et al., 1999.

In a continuation of this analysis, we studied the interaction domain in STRAP for p300. An analysis of the same set of STRAP mutant derivatives indicated that the predominant p300 interaction domain was, in contrast, localised in the C-terminal half of STRAP, and encompassed from residue 206 to 438. Overall, these binding studies established that STRAP possesses two separable and distinct regions of interaction for JMY and p300, the binding domain for JMY being primarily localised within the N-terminal half with the p300 interaction domain being present in the C-terminal half (FIG. 7).

A similar approach was taken to elucidate the domains in JMY and p300 that are responsible for interacting with STRAP. An analysis of the binding properties of a panel of in vitro translated JMY derivatives indicated that JMY harbours at least two interaction domains for STRAP, one of which resides within the N-terminal 119 residues, the other being broadly defined to the C-terminal region from residue 683 to 983. In addition, another STRAP binding domain in JMY mapped to residue 468 to 558, as this region was used in the two-hybrid screen to isolate STRAP. Thus, JMY contains at least three distinct interaction domains for STRAP (FIG. 7).

Finally, we investigated a panel of p300 derivatives for their STRAP binding activity. As expected, wild-type p300 bound to STRAP, and further analysis of the binding properties of the mutant derivatives mapped two p300 interaction domains, one to the N-terminal 595 residues, with the other one located in the C-terminal region between residues 1572 to 1921. Taken together, this analysis of the binding properties of STRAP, JMY and p300 established that STRAP can bind specifically to JMY and p300, and that it does so through distinct domains within the N- and C-terminal regions of the protein (see FIG. 7). Similarly, JMY and p300 possess dedicated domains that allow each protein to interact with STRAP and, as previously documented, with each other.

STRAP Facilitates the Interaction Between JMY and p300.

The level of JMY that co-immunoprecipitated with p300 from cells transfected with JMY and p300 was determined, and thereafter the effect of co-expressing STRAP. At the same time, we investigated the level of JMY, p300 and STRAP in transfected cells which indicated that co-expressing STRAP, p300 and JMY caused an accumulation of JMY and STRAP. In the same cell extract we found, as expected (Shikama et al., 1999), that JMY co-immunoprecipitated with p300 and, importantly, that there was a highly significant increase in the level of JMY in the p300 immunocomplex in the presence of STRAP. Moreover, since the amount of p300 in the immunocomplex was similar in the absence or presence of STRAP, the increased level of co-immunoprecipitated JMY results from the influence of STRAP on the recruitment of JMY into the p300 complex.

Figure 8:
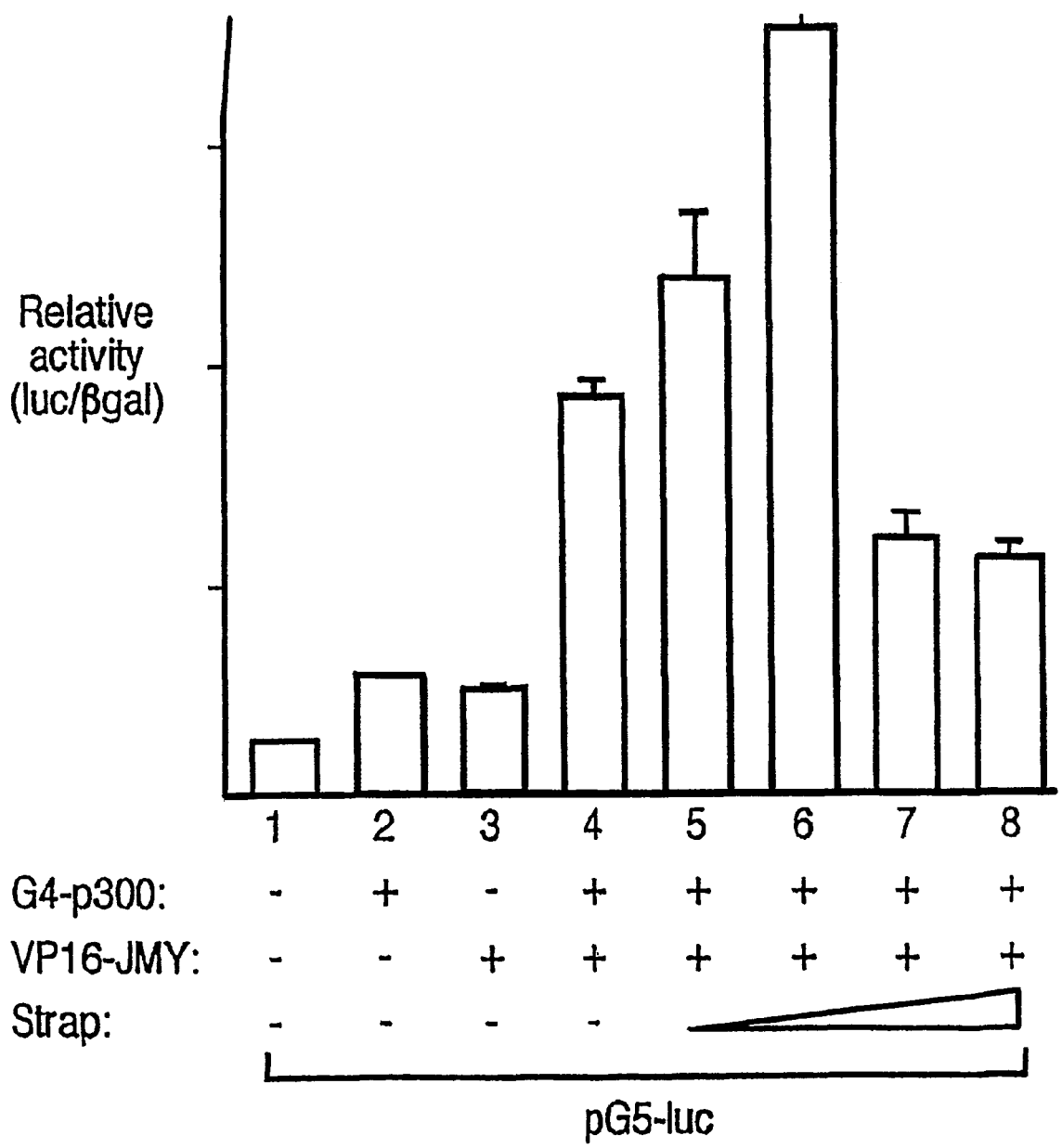
FIG. 8 shows the results of a two-hybrid assay performed in U2OS cells with pG4-p300 (50 ng) and pVP-16-JMY (250 ng) in the presence of increasing amounts of pHA-Strap (0.5, 1.0, 3.0 and 5.0 μg), together with the reporter pG5-luc (1 μg) and internal control pCMV-βgal (1 μg). The data represent the relative activity of luciferase to β-galactosidase and are the average values derived from two or more different readings.

A mammalian two-hybrid assay was used to investigate whether STRAP affected the interaction between JMY and p300. As in previous studies, in a two-hybrid assay G4-p300 and VP16-JMY could interact with each other (Shikama et al., 1999). Under these conditions, STRAP caused a significant increase in activity. A titration of STRAP indicated that further increases in the amount of co-transfected STRAP caused a reduction in the two-hybrid signal (FIG. 8). A possible explanation for this phenomenon is that there is an optimal level of STRAP that favours the interaction between JMY and p300, above which the level of STRAP out-titrates the amount of p300 and JMY, and rather than recruiting p300 and JMY into a ternary complex, STRAP binds to each as heterodimer and thus interferes with the two-hybrid interaction.

We then purified recombinant p300, JMY and STRAP and studied the influence of STRAP upon the interaction between JMY and p300 in a biochemical assay. Previous studies have established that JMY and p300 can form a protein complex, and identified the domains in each protein that are responsible for this interaction (Shikama et al., 1999). Under conditions where purified recombinant p300 and JMY could weakly bind to each other, the addition of STRAP increased the efficiency of their interaction, enhancing the amount of JMY that bound to p300. The specificity of this effect was established through a variety of control treatments, including the effect of a STRAP mutant derivative containing the N-terminal region (residue 8 to 123), that harbours one complete TPR motif, and is capable of binding to JMY, but not p300 (FIG. 7). The addition of a similar amount of STRAP8-123 failed to affect the interaction between. p300 and JMY, thus establishing the specific effect of STRAP on the JMY/p300 interaction.

STRAP Augments the p53 Response.

It is known that p300/CBP proteins participate in the control of p53-dependent transcription, and that during the p53 response altered p53 stability serves as a major level of regulation through a process which perhaps involves p300 (Ko and Prives, 1997; Levine et al., 1997; Shikama et al., 1997). We introduced STRAP into U2OS cells and studied the level of endogenous p53 by immunoblotting. Increasing the levels of STRAP caused a concomitant increase in p53. Similarly, upon the introduction of exogenous p53 into p53−/− MEFs, we observed a significant increase in p53 levels. Mutant derivatives of STRAP representing both N-and C-terminal deletions failed to cause any alteration in p53 level. We introduced STRAP into U2OS cells to test for any effect on the half-life of p53 and studied endogenous p53 after treating the cells with cyclohexamide. We found that endogenous p53 had a half-life of about 30 minutes which, upon the expression of STRAP, was significantly lengthened to about 240 minutes. In contrast, the expression of neither JMY nor p300 had a significant impact on p53 half-life, which remained at approximately 30 minutes. Thus, STRAP induces the p53 protein, which it does so in part by altering the rate of p53 turnover and increasing p53 half-life.

Previous studies have established that the physical interaction of MDM2 with the activation domain of p53 abrogates the p53 response by targeting p53 for degradation (Haupt et al., 1997; Kubbutat et al., 1997). Thus, the level of exogenous p53 in p53−/− MEFs was reduced upon the co-expression of human MDM2 (referred to as hDM2).

Under these conditions, the presence of STRAP significantly increased the level of p53, providing indication that STRAP can override the down-regulation of p53 activity by hDM2, a result that is consistent with the ability of STRAP to extend p53 half-life and augment the levels of the p300 co-activator complex. It is important to note that under these experimental conditions we failed to detect any direct interaction between p53 and STRAP.

Figure 9:
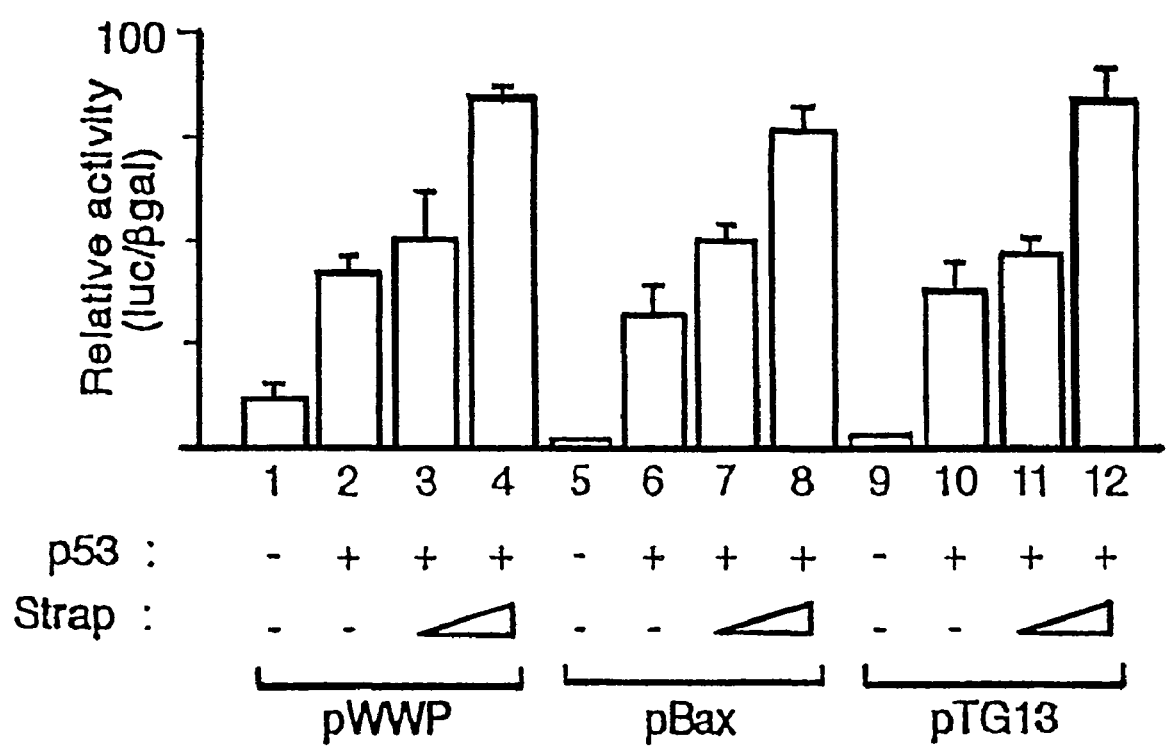
FIG. 9 shows the indicated p53 reporter constructs, pWWP-luc, pBax-luc and pTG13 (1 μg) together with expression vectors for p53 (0.025 μg) and Strap (2 μg and 5 μg) were transfected into SAOS2 cells as indicated. The values shown represent the average of three separate readings and are the relative level of luciferase to β-galactosidase derived from the internal control.

As p300/CBP and JMY are involved in regulating p53 transcriptional activity, we investigated the effect of STRAP on different p53-responsive promoters. Consistent with its presence in the p300 co-activator complex and the ability to extend p53 half-life, we found STRAP to be capable of inducing p53 activity on a variety of different p53-responsive promoters, including waf1, bax and the artificial p53-responsive TG13 promoter (FIG. 9).

Figure 10:
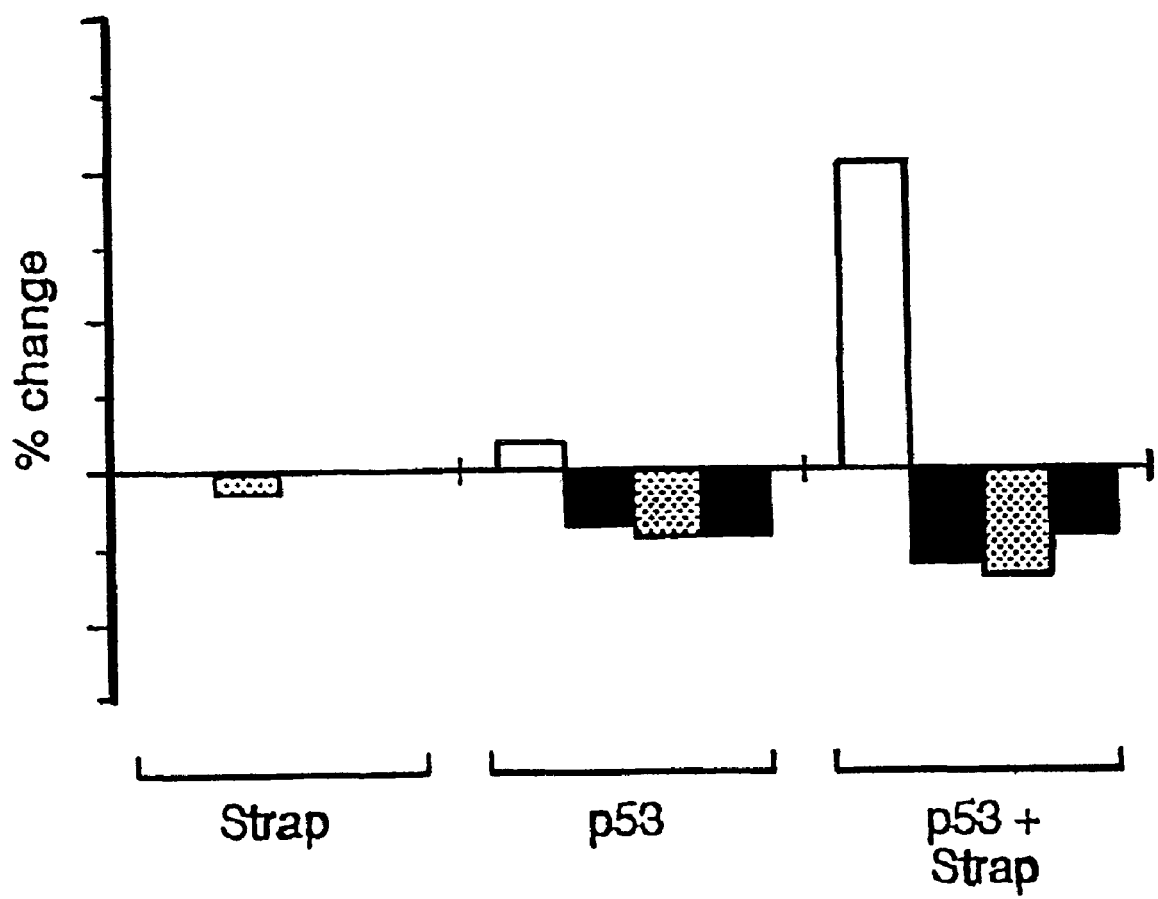
FIGS. 10 and 11 show the results of SAOS2 cells transfected with expression vectors for wild-type p53 or p5322/23 (4 μg) in the presence or absence of Strap (7 μg) together with pCMV CD20 (7 μg), as indicated. At 36 h after transfection, transfected cells were identified by staining with anti-CD20 antibody, and DNA was stained with propidium iodide, and the proportion of sub-G1, G1, S and G2/M phase cells determined as described. The % change in the size of the sub-G1, G1, S and G2/M population is shown. p53 caused about 37% of the transfected cells to enter apoptosis, compared to 17% with the vector alone.

We then investigated whether the ability of STRAP to increase p53 protein levels and augment transcription correlated with the physiological properties of p53, namely the ability to promote cell cycle arrest and apoptosis (Levine, 1997). In SAOS2 (p53-/-) tumour cells we identified conditions where the introduction of wild-type p53 caused a low but significant increase in the population of apoptosing cells (FIG. 10). Under these conditions, co-expressing STRAP with p53 resulted in a marked increase in the size of the apoptosing cell population, in contrast to the effects of STRAP in the absence of p53, which were minimal. These results establish that STRAP augments the apoptotic activity of p53.

Figure 11:
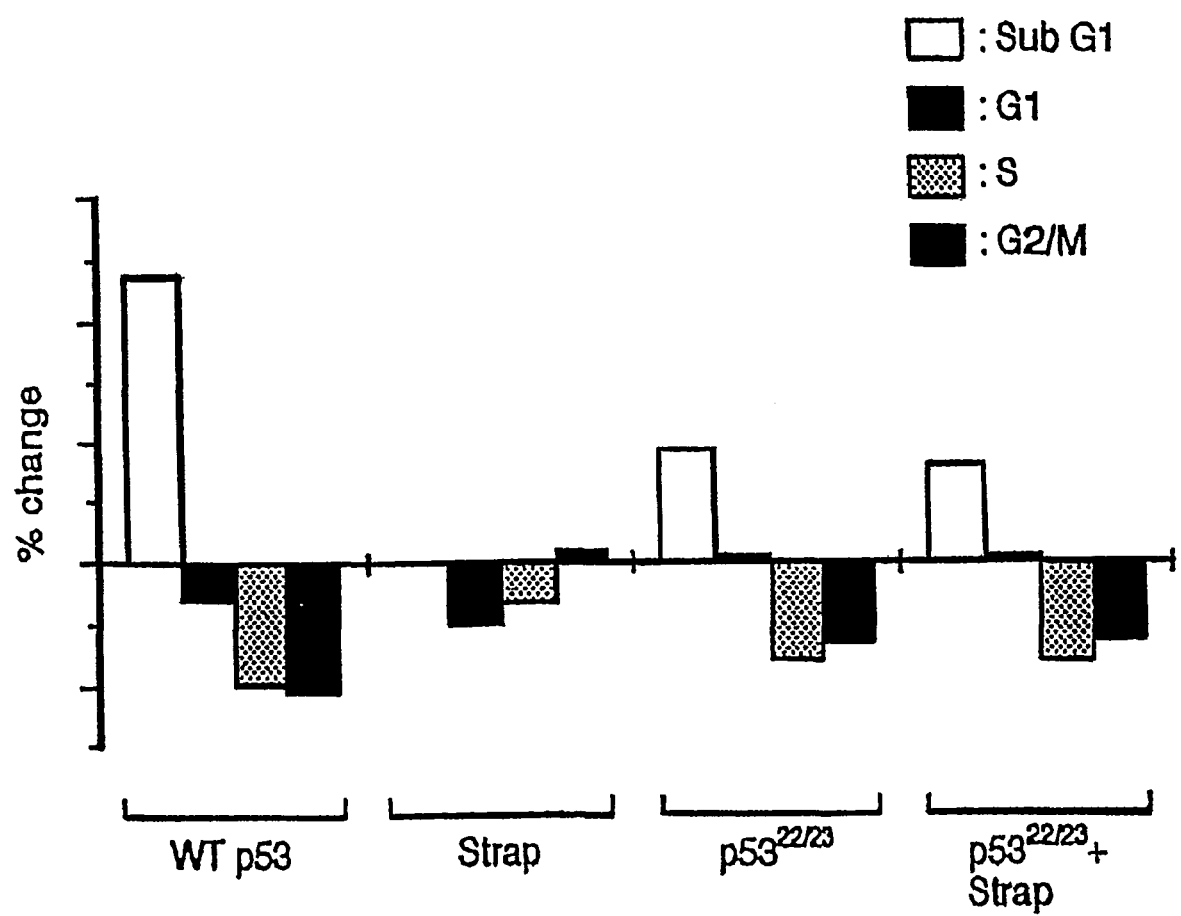

The presence of STRAP in the p300 co-activator complex provided indication that STRAP can augment p53-dependent apoptosis through stimulating p53 transcriptional activity. We assessed whether STRAP could induce p5322/23, which is a mutant p53 derivative that has two residues altered in the activation domain, and which is severely compromised in transcriptional activity (Lin et al., 1994). In comparison to wild-type p53, p5322/23 was less efficient at inducing apoptosis but still retained a significant level of activity (FIG. 11). However, in contrast to wild-type p53, the apoptotic activity of p5322/23 was not affected by co-expressing STRAP, a result that is consistent with a role for STRAP in stimulating p53 transcription.

Overall, these studies provide indication that STRAP as a component of the p300 co-activator complex induces p53 activity in part by increasing the stability of the p53 protein, and further that this effect directly influences p53-dependent transcription and therefore the p53 response.

STRAP is a Damage-responsive Component of the p300 Co-activator Complex.

Figure 12:
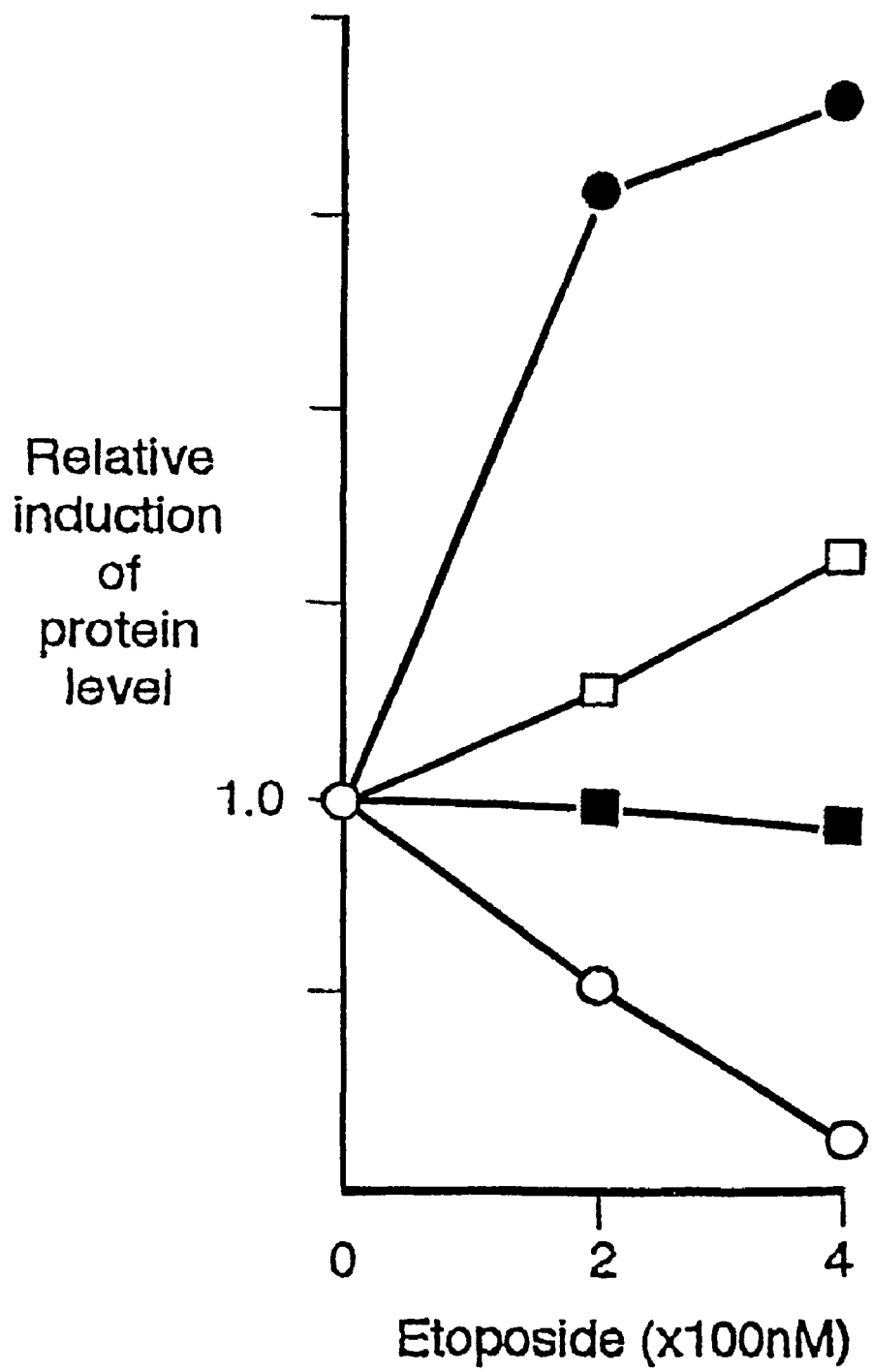
FIG. 12 shows the results of COS cells transfected with either pHA-Strap (5 μg), pCMV-JMY (5 μg) or pCMV-NAP2 (5 μg) and treated as described either with or without etoposide (200 or 400 nM). The levels of exogenous Strap, JMY and NAP, and endogenous p53, were determined by immunoblotting with the relevant antibodies, quantitated by phosphoimaging and thereafter presented graphically. The level of protein detected in the non-treated cell was given an arbitrary value of 1.0. The symbols indicate: • p53, □ Strap, ■ JMY and ○ NAP.

We investigated whether the protein level was altered in stressed cells by studying the effect of etoposide, which is an agent that can efficiently induce the p53 response (Kaufmann, 1998; Arriola et al., 1999). We compared in U2OS cells the induction of STRAP to p53, as well as to the induction of JMY and NAP (nucleosomal assembly protein), the latter serving as a control protein that was un likely to be affected by stress. STRAP protein levels increased in response to etoposide, although not as dramatically as observed for p53; in contrast, JMY and NAP failed to undergo a similar response, with NAP levels declining (FIG. 12).

We then investigated the p300/JMY complex in etoposide-treated U2OS cells, in the absence and presence of STRAP. The expression of STRAP caused an increase in the level of JMY bound to p300, which showed a further and significant increase upon treating the cells with etoposide. Using the same cell extracts, a marked increase in the level of co-immunoprecipitated JMY with p300 was observed when STRAP expressing cells were treated with etoposide (usually about 10-fold in contrast to 2-fold induction of protein level). These results provide indication that STRAP is a stress responsive protein that augments the interaction between p300 and JMY.

Figure 13:
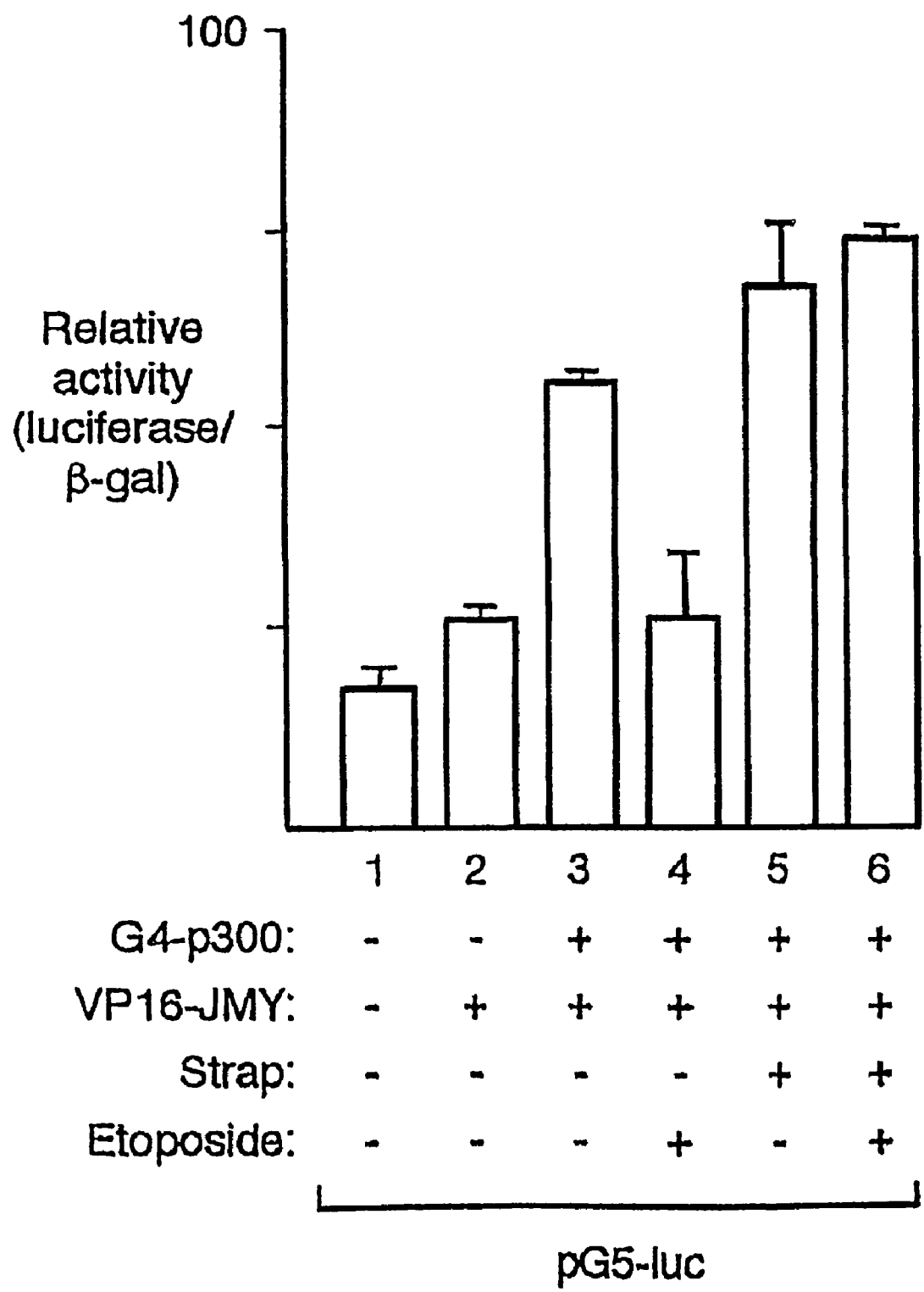
FIG. 13 shows a two-hybrid assay performed in U2OS cells with pG4-p300 (100 ng) and pVP16-JMY (1 μg) in the presence of pHA-Strap (2.5 μg) and etoposide (200 nM) as indicated, and the reporter pG5-luc (1 μg) and internal control pCMV-βgal (1 μg). The data represent the relative activity of luciferase to β-galactosidase, and are the average values derived from two different readings.

The role of STRAP in regulating the stress-responsive interaction between p300 and JMY was further characterised in a two-hybrid assay using G4-p300 and VP16-JMY. We found that treating U2OS cells with etoposide (200 nM) caused a marked reduction in the level of two-hybrid signal, and that the expression of STRAP completely restored two-hybrid activity (FIG. 13). This effect required the integrity of the STRAP protein, as a mutant derivative that failed to interact with p300 but retained the ability to bind to JMY, STRAP8-205, could not overcome the effect of etoposide upon the two-hybrid interaction between G4-p300 and VP16-JMY.

Figure 14:
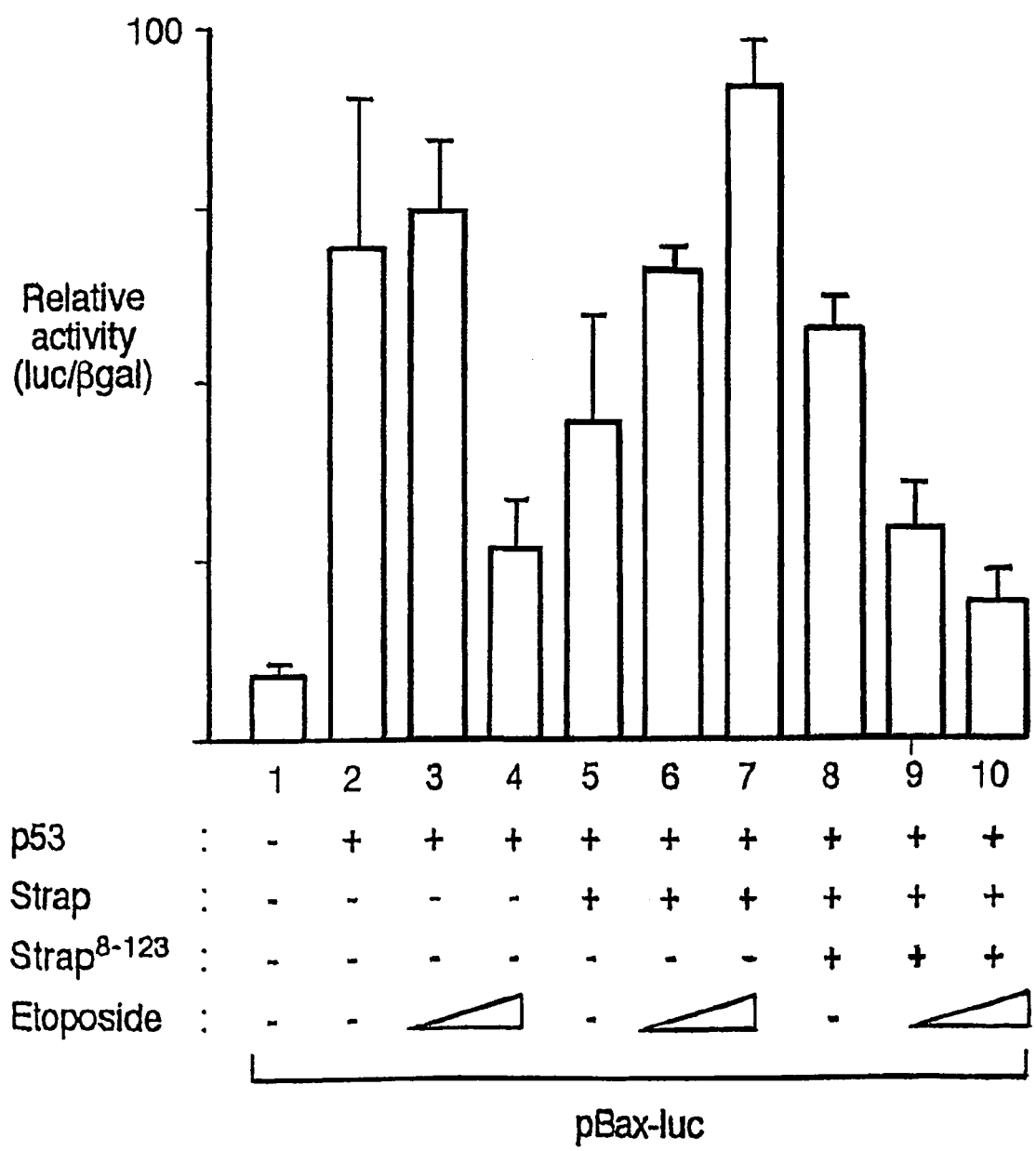
FIG. 14 shows SAOS2 cells transfected with expression vectors for Strap or Strap8-123 (4 μg) and treated with etoposide (100 and 200 nM) as indicated. Exogenous p53 transcriptional activity was measured using pBax-luc (1 μg), which was co-transfected together with expression vectors for p53 (0.025 μg) and the internal control pCMV-βgal (1 μg). The values shown represent the average of three separate readings and are the relative level of luciferase.

We extended these studies to an analysis of the effect of STRAP upon the etoposide-dependent regulation of wild-type p53 transcriptional activity. In a similar fashion to the etoposide effect on the p300/JMY interaction (FIG. 13), at a high concentration of etoposide, a reduction in p53 activity occurred (FIG. 14). Co-expression of STRAP partially overcame the etoposide-dependent down-regulation of p53 transcriptional activity and furthermore, the effect of STRAP was dependent upon the integrity of the wild-type protein, since the expression of STRAP8-123 interfered with wild-type STRAP activity, most probably through a dominant-negative type of effect (FIG. 14).

These results provide indication that STRAP plays a direct role in facilitating the p53 response in conditions of cellular stress. A far greater association was observed between STRAP and the p53 transcription complex in etoposide-treated U2OS cells compared to untreated cells, indicating that the association between STRAP and p300, and thereafter p53, is stress-responsive. These results demonstrate that STRAP functions in regulating and maintaining p300 co-activator function during cellular stress, and that this role of STRAP contributes to p53 activity.

Endogenous STRAP is a Stress-responsive Protein.

The stress responsiveness of endogenous STRAP was determined stress using the anti-STRAP peptide antibody by studying. STRAP levels in A31 cells after treatment with etoposide, as well as other stress-inducing agents. STRAP was found to be effectively induced by etoposide whereas the effect of ultra-violet light and ionizing radiation was less marked.

The importance of p53 and MDM2 in the stress-regulation of endogenous STRAP was assessed by monitoring STRAP levels in early passage p53-/- or p53-/-/mdm2-/- mouse embryo fibroblasts (MEFs). STRAP was induced in p53-/- MEFs to a similar extent as that observed in murine A31 cells. In contrast, little change in STRAP level was observed in the double knockout p53-/-/mdm2-/- cells. These results show that STRAP can be induced independently of p53, but indicate that MDM2 can influence the stress-responsive induction of STRAP.

The stress response control of STRAP described herein allows a number of important conclusions to be made. Firstly, STRAP is a stress-responsive protein, since STRAP levels increased in stressed cells. Secondly, the effect and interaction of STRAP with the p53 associated p300 complex provide strong indication that STRAP is a functionally important component of the p53 response. The latter conclusion, in combination with the earlier results on the ability of STRAP to foster the interaction between p300 and JMY, show that a primary function of STRAP is to augment p300 co-activator activity in conditions of the p53 response.

STRAP is a Novel TPR Motif Protein.

The characterisation of STRAP has shown that the protein possesses a rather unusual domain organisation, since it is composed almost entirely of a tandem series of TPR motifs (Lamb et al., 1995). The TPR motif has been found in a wide variety of proteins, from prokaryotes to eukaryotes, and is generally believed to represent an ancient protein-protein interaction module (Blatch and Lassle, 1999). Proteins that contain TPR motifs function in diverse physiological processes, including the cell cycle, transcription and the stress response, where they usually occur as integral components of multiprotein complexes.

The characteristics ascribed to STRAP as a functionally important component involved in regulating the p300/CBP co-activator complex fit very well with the generic properties previously assigned to TPR motif-containing proteins in regulating and mediating the assembly of macromolecular protein complexes. Particularly relevant is the considerable body of evidence that highlights the multicomponent nature of p300/CBP co-activator complex, in which STRAP plays a role in facilitating the interaction between p300 and JMY (Shikama et al., 1999). Another notable feature is the fact that STRAP has distinct and separable TPR motif-containing domains that allow it to bind to protein components of the p300 co-activator complex. Moreover, our results imply that this ability of STRAP to interact with p300 and JMY facilitates their interaction, suggesting that STRAP may play a role in maintaining the functional integrity of the p300/CBP co-activator complex.

STRAP May Facilitate the Assembly of the p300/CBP Co-activator Complex.

It is interesting to speculate on the role of STRAP in the p300/CBP co-activator complex. In this respect, it is noteworthy that although proteins with multiple TPR motifs are found in other protein complexes, the TPR motif usually co-exists with domains dedicated to other functions, such as phosphatase activity in the case of PP5 (Ollendorf and Donoghue, 1997). STRAP is unusual in this respect, as the majority of the protein exists as a series of tandem TPR motifs.

STRAP can interact specifically with JMY and p300, using domains which at the biochemical level appear to be non-overlapping. Previous studies indicated that JMY and p300 can directly and specifically bind to each other (Shikama et al., 1999), an interaction that STRAP enhances through a process that involves the formation of a ternary complex between STRAP, p300 and JMY. STRAP may play a role in regulating the assembly of the p300 complex, and represents a key regulatory component in controlling p300 co-activator activity.

STRAP is Stress-responsive and Augments the p53 Response.

Figure 15:
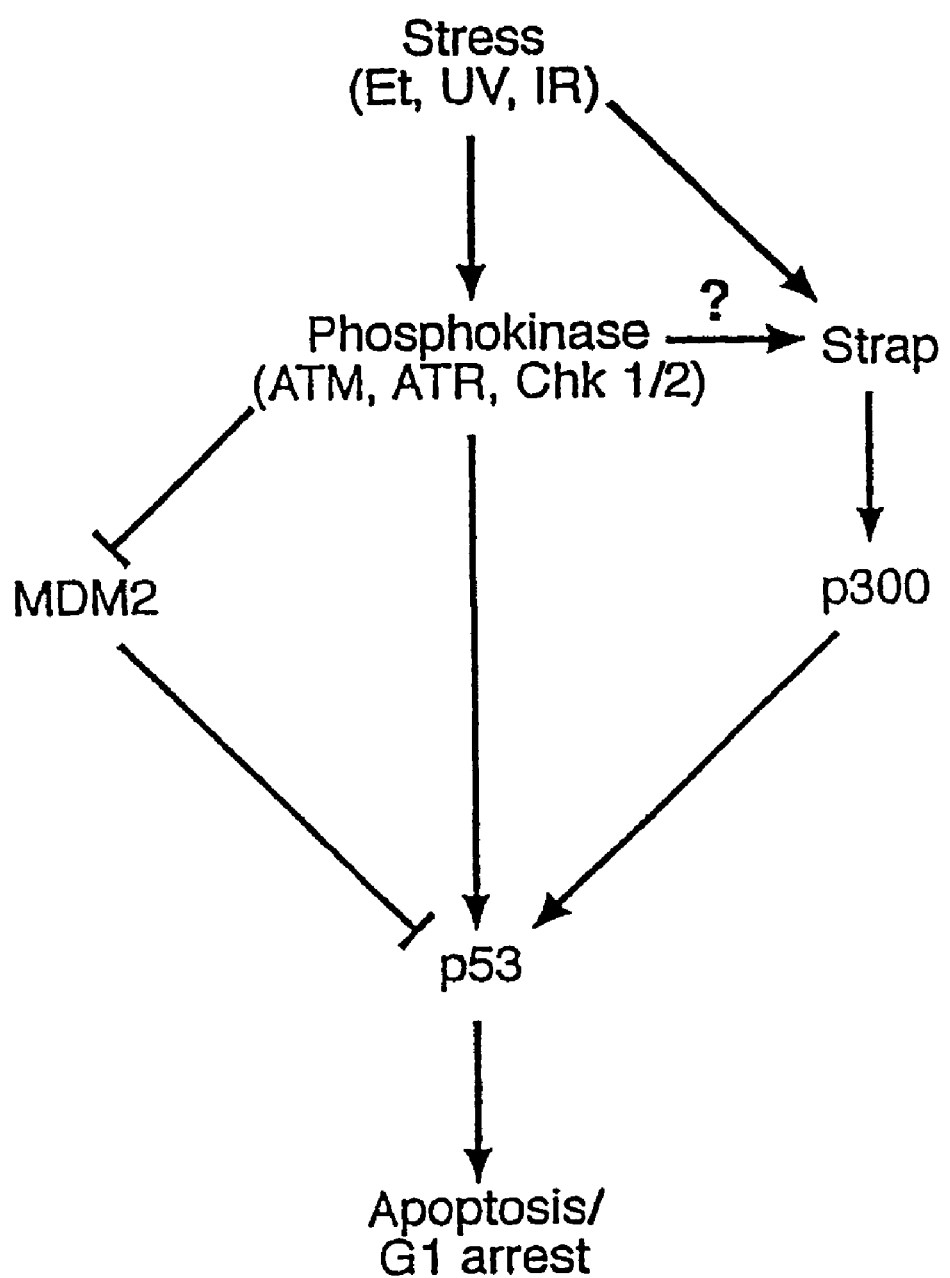
FIG. 15 shows a possible model for role of Strap in the p53 response. Strap is induced by stress, and activates p300 co-activator function. As a result, the p53 response is triggered to cause apoptosis or G1 arrest. Stress activated phosphokinases (including ATM, ATR and chk½) act upon p53 and MDM2 to alter p53 stability and enhance the interaction of p53 with the p300 co-activator complex. Strap is induced by stress (? indicates that it is not known whether the same phosphokinases are involved) and augments the activity of the p300 co-activator complex by facilitating co-factor interactions.

STRAP induces p53-dependent transcription and facilitates the p53 response (FIG. 15). Given the documented role of the p300 co-activator complex in regulating p53 activity (Gu et al., 1997; Lill et al., 1997; Lee et al., 1998), this activity may result from the ability of STRAP to foster the assembly of the p300 co-activator complex during cellular stress. In its regulation of p53, an important property was seen in the level of the STRAP protein, which undergoes a stress-responsive accumulation when cells were treated with agents such as etoposide, which is known to activate the p53 response by causing double stranded breaks in genomic DNA (Kaufman, 1998). Thus, our study provides indication that there are a number of steps through which STRAP influences the p53 response, whereby the initiating event, namely the STRAP facilitated assembly of the p300 co-activator complex contributes to a variety of downstream consequences, including an extended p53 half-life, in part through modulating MDM2 activity, and thereafter the activation of p53 target genes that execute the p53 response.

A New Level of Control in the p53 Response.

This document describes the first transcription co-factor that has a dedicated role in regulating the assembly of a transcriptional co-activator complex and which, furthermore, possesses molecular properties which allow it to function during cellular stress. The properties of STRAP are well-suited to this role. STRAP favours and strengthens complex formation between p300 and JMY, and undergoes stress-responsive protein accumulation. These properties endow STRAP with the ability to maintain p300 co-activator activity in adverse cellular conditions. The properties of STRAP may have an important impact on facilitating the cellular stress response which, in the case of the p53 response, relies upon the transcriptional activation of a set of targets genes that act as a major driving force in delivering and executing the response mechanism.

REFERENCES

Arriola, E. L. et al (1999) Oncogene 18, 1081-1091.
Avantaggiati, M. L. et al-(1997) Cell 89, 1175-1184.
Bannister, A. J. and Kouzarides, T. (1996) Nature 384, 641-643.
Blatch, G. L. and Lassle, M. (1999) Bioessays 21, 932-939.
Bose, S. et al (1996) Science 274, 1715-1717.
Buck, V. et al (1995) Oncogene 11, 31-38.
Chehab, N. B. et al (2000) Genes Dev. 14, 278-288.
Chen, S. et al (1996) Mol. Endocrinol. 10, 682-693.
Cho, Y. et al (1994) Science 265, 346-355.
Das, A. K. et al (1998) EMBO J. 17, 1192-1199.
de la Luna, S. et al (1999) EMBO J. 18, 212-228.
Eckner, R., et al. Genes Dev. 8, 869-884 (1994).
El-Deiry, W. S. et al (1993) Cell 75, 817-825.
Giaccia, A. J. and Kastan, M. B. (1998) Genes Dev. 12, 22973-2983.
Greenblat, M. S. (1994) Cancer Res. 54, 4855-4878.
Grossman, S. R. et al (1998) Mol. Cell 2, 405-415.
Gu, W. et al (1997) Nature 387, 819-822.
Gu, W. and Roeder, R. G. (1997) Cell 90, 595-606.
Haupt, Y. et al (1997) Nature 387, 296-299.
Honda, R. et al (1997) FEBS Lett. 420, 25-27.
Kaufmann, S. H. (1998) Biochim. Biophys. Acta 1400, 195-211.
Keleher, C. A. et al (1992) Cell 68, 709-719.
Khosravi, R. et al (1999) Proc. Natl. Acad. Sci. 96, 14973-14977;
Ko, L.-J. and Prives, C. (1996) Genes Dev. 10, 1054-1072.
Kubbutat, M. H. G. et al (1997). Nature 387, 299-303.
Lakin, N. D. and Jackson, S. P. (1999) Oncogene 18, 7644-7655.
Lamb, J. R. et al (1994) EMBO J. 13, 4321-4328.
Lamb, J. R. et al (1995) TIBS 20, 257-259.
Lässle, M. et al (1997.) J. Biol. Chem. 272, 1876-1884.
Lee, C-W. et al (1998) Oncogene 16, 2695-2710.
Levine, A. J. (1997) Cell 88, 323-331.
Lill, N. L. et al (1997) Nature 387, 823-827.
Lin, J. et al (1994) Genes Dev. 8, 1235-1246.

Loughran, Ö. and La Thangue, N. B. (2000) Mol. Cell. Biol. 20, 2186-2197.
Maki, C. G. and Howley, P. M. (1997) Mol. Cell. Biol. 17, 355-363.
Miyashita, T. and Reed, J. C. (1995) Cell 80, 293-299.
Oliner, J. D. et al (1993) Nature 362, 857-860.
Ollendorff, V. and Donoghue, D. J. (1997) J. Biol. Chem. 272, 32011-32018.
Piette, J. et al (1997) Oncogene 15, 1001-1010.
Russell, L. C. et al (1999) J. Biol. Chem. 274, 20060-20063.
Sakaguchi, K. et al (1998) Genes Dev. 12, 2831-2841.
Scheufler, C. et al (2000) Cell 101, 199-210.
Schiltz, R. L. and Nakatani, Y. (2000) Biochem. Biophys. Acta. 1470, 37-53.
Sheih, S.-Y. et al (1997) Cell 91, 325-334.
Shieh, S.-Y. et al (2000) Genes Dev. 14, 289-300.
Shikama, N. et al (1997) Trends Cell Biol. 7, 230-236.
Shikama, N. et al (1999) Molecular Cell 4, 365-376.
Shikama, N. et al (2000) Submitted.
Silverstein, A. M. et. al (1997) J. Biol. Chem. 272, 18467-18472.
Sinclair, C. et al (1999) J. Biol. Chem. 274, 23666-23672.
Smith R. L. et al (1995) Genes Dev. 9, 2903-2910.
Sørensen, T. S. et al (1996) Mol. Cell. Biol. 16, 5888-5895.
Tibbetts, R. S. et al (1999) Genes Dev. 13, 152-157.
Tzamarias, D. and Struhl, K. (1994) Nature 369, 758-761.
Tzamarias, D. and Struhl, K. (1995) Genes Dev. 9, 821-831.
Vojtek, A. B. et al (1993) Cell 74, 205-214.
Wu, X. et al (1993) Genes Dev. 7, 1126-1132.
Young, J. C. et al (1998) J. Biol. Chem. 273, 18007-18010.
Yuan, Z.-M. et al (1999) J. Biol. Chem. 274, 1883-1886.
Zamanian, M. and La Thangue, N. B. (1992) EMBO J. 11, 2603-2610.

The invention claimed is:

1. An isolated polypeptide which includes the amino acid sequence shown in SEQ ID NO:1 or the amino acid sequence shown in SEQ ID NO:2.

2. A peptide which binds JMY and/or p300 and is capable of modulating p53 activity, said peptide being a fragment of an isolated polypeptide which includes the amino acid sequence shown in SEQ ID NO:1 or the amino acid sequence shown in SEQ ID NO:2.

3. An isolated nucleic acid molecule encoding the polypeptide as shown in SEQ ID NO:2.

4. An expression vector comprising the nucleic acid according to claim 3 operably linked to a regulatory sequence.

5. An isolated host cell transformed with the expression vector of claim 4.

6. A pharmaceutical composition comprising a polypeptide or peptide fragment according to claim 1 or 2 and a pharmaceutically acceptable excipient or carrier.

7. A method of making a polypeptide which includes the amino acid sequence shown in SEQ ID NO:2 comprising culturing a host cell transformed with an expression vector, said vector comprising a nucleic acid molecule encoding a polypeptide shown in SEQ ID NO:2, said nucleic acid being operably linked to a regulatory sequence, said culturing comprising conditions for expression of said polypeptide.

8. The method of making a polypeptide according to claim 7, comprising testing for binding for JMY or p300.

9. The method according to claim 7, further comprising isolating and/or purifying said polypeptide.

10. The method according to claim 9 wherein the isolated or purified polypeptide is formulated into a composition comprising one or more additional components.

11. An assay method for obtaining an agent able to interact with a polypeptide or fragment according to claim 1 or claim 2, including:
(i) bringing into contact said polypeptide or fragment and a putative binding molecule or other test substance; and
(ii) determining interaction or binding between the polypeptide or fragment and the test substance.

* * * * *

SEQUENCE LISTING

```
<160> NUMBER OF SEQ ID NOS: 9

<210> SEQ ID NO 1
<211> LENGTH: 440
<212> TYPE: PRT
<213> ORGANISM: Mus sp.

<400> SEQUENCE: 1

Met Met Ala Asp Glu Glu Glu Ala Lys His Val Leu Gln Lys Leu
 1               5                  10                  15

Gln Gly Leu Val Asp Arg Leu Tyr Cys Phe Arg Asp Ser Tyr Phe Glu
                20                  25                  30

Thr His Ser Val Glu Asp Ala Gly Arg Lys Gln Gln Asp Val Gln Glu
            35                  40                  45

Glu Met Glu Lys Thr Leu Gln Gln Met Glu Glu Val Leu Gly Ser Ala
        50                  55                  60

Gln Val Glu Ala Gln Ala Leu Met Leu Lys Gly Lys Ala Leu Asn Val
    65                  70                  75                  80

Thr Pro Asp Tyr Ser Pro Glu Ala Glu Val Leu Leu Ser Lys Ala Val
                85                  90                  95

Lys Leu Glu Pro Glu Leu Val Glu Ala Trp Asn Gln Leu Gly Glu Val
                100                 105                 110

Tyr Trp Lys Lys Gly Asp Val Thr Ser Ala His Thr Cys Phe Ser Gly
            115                 120                 125

Ala Leu Thr His Cys Lys Asn Lys Val Ser Leu Gln Asn Leu Ser Met
        130                 135                 140

Val Leu Arg Gln Leu Gln Thr Asp Ser Gly Asp Glu His Ser Arg His
    145                 150                 155                 160

Val Met Asp Ser Val Arg Gln Ala Lys Leu Ala Val Gln Met Asp Val
                165                 170                 175

Leu Asp Gly Arg Ser Trp Tyr Ile Leu Gly Asn Ala Tyr Leu Ser Leu
            180                 185                 190

Tyr Phe Asn Thr Gly Gln Asn Pro Lys Ile Ser Gln Gln Ala Leu Ser
        195                 200                 205

Ala Tyr Ala Gln Ala Glu Lys Val Asp Arg Lys Ala Ser Ser Asn Pro
    210                 215                 220

Asp Leu His Leu Asn Arg Ala Thr Leu His Lys Tyr Glu Glu Ser Tyr
    225                 230                 235                 240
```

```
Gly Glu Ala Leu Glu Gly Phe Ser Gln Ala Ala Leu Asp Pro Ala
            245                 250                 255

Trp Pro Glu Pro Gln Gln Arg Glu Gln Gln Leu Leu Glu Phe Leu Ser
        260                 265                 270

Arg Leu Thr Ser Leu Leu Glu Ser Lys Gly Lys Thr Lys Pro Lys Lys
            275                 280                 285

Leu Gln Ser Met Leu Gly Ser Leu Arg Pro Ala His Leu Gly Pro Cys
    290                 295                 300

Gly Asp Gly Arg Tyr Gln Ser Ala Ser Gly Gln Lys Met Thr Leu Glu
305                 310                 315                 320

Leu Lys Pro Leu Ser Thr Leu Gln Pro Gly Val Asn Ser Gly Thr Val
                325                 330                 335

Val Leu Gly Lys Val Val Phe Ser Leu Thr Thr Glu Glu Lys Val Pro
            340                 345                 350

Phe Thr Phe Gly Leu Val Asp Ser Asp Gly Pro Cys Tyr Ala Val Met
        355                 360                 365

Val Tyr Asn Val Val Gln Ser Trp Gly Val Leu Ile Gly Asp Ser Val
    370                 375                 380

Ala Ile Pro Glu Pro Asn Leu Arg His His Gln Ile Arg His Lys Gly
385                 390                 395                 400

Lys Asp Tyr Ser Phe Ser Ser Val Arg Val Glu Thr Pro Leu Leu Leu
                405                 410                 415

Val Val Asn Gly Lys Pro Gln Asn Ser Ser Ser Gln Ala Ser Ala Thr
            420                 425                 430

Val Ala Ser Arg Pro Gln Cys Glu
        435                 440

<210> SEQ ID NO 2
<211> LENGTH: 440
<212> TYPE: PRT
<213> ORGANISM: Homo sapiens

<400> SEQUENCE: 2

Met Met Ala Asp Glu Glu Glu Val Lys Pro Ile Leu Gln Lys Leu
 1               5                  10                  15

Gln Glu Leu Val Asp Gln Leu Tyr Ser Phe Arg Asp Cys Tyr Phe Glu
            20                  25                  30

Thr His Ser Val Glu Asp Ala Gly Arg Lys Gln Gln Asp Val Arg Lys
        35                  40                  45

Glu Met Glu Lys Thr Leu Gln Gln Met Glu Glu Val Val Gly Ser Val
    50                  55                  60

Gln Gly Lys Ala Gln Val Leu Met Leu Thr Gly Lys Ala Leu Asn Val
65                  70                  75                  80

Thr Pro Asp Tyr Ser Pro Lys Ala Glu Glu Leu Leu Ser Lys Ala Val
                85                  90                  95

Lys Leu Glu Pro Glu Leu Val Glu Ala Trp Asn Gln Leu Gly Glu Val
            100                 105                 110

Tyr Trp Lys Lys Gly Asp Val Ala Ala His Thr Cys Phe Ser Gly
        115                 120                 125

Ala Leu Thr His Cys Arg Asn Lys Val Ser Leu Gln Asn Leu Ser Met
    130                 135                 140

Val Leu Arg Gln Leu Arg Thr Asp Thr Glu Asp Glu His Ser His His
145                 150                 155                 160

Val Met Asp Ser Val Arg Gln Ala Lys Ser Ala Val Gln Met Asp Val
                165                 170                 175
```

-continued

His Asp Gly Arg Ser Trp Tyr Ile Leu Gly Asn Ser Tyr Leu Ser Leu
                180                 185                 190

Tyr Phe Ser Thr Gly Gln Asn Pro Lys Ile Ser Gln Gln Ala Leu Ser
            195                 200                 205

Ala Tyr Ala Gln Ala Glu Lys Val Asp Arg Lys Ala Ser Ser Asn Pro
        210                 215                 220

Asp Leu His Leu Asn Arg Ala Thr Leu His Lys Tyr Glu Glu Ser Tyr
225                 230                 235                 240

Gly Glu Ala Leu Glu Gly Phe Ser Arg Ala Ala Leu Asp Pro Ala
                245                 250                 255

Trp Pro Glu Pro Arg Gln Arg Glu Gln Gln Leu Leu Glu Phe Leu Asp
                260                 265                 270

Arg Leu Thr Ser Leu Leu Glu Ser Lys Gly Lys Val Lys Thr Lys Lys
            275                 280                 285

Leu Gln Ser Met Leu Gly Ser Leu Arg Pro Ala His Leu Gly Pro Cys
        290                 295                 300

Ser Asp Gly His Tyr Gln Ser Ala Ser Gly Gln Lys Val Thr Leu Glu
305                 310                 315                 320

Leu Lys Pro Leu Ser Thr Leu Gln Pro Gly Val Asn Ser Gly Ala Val
                325                 330                 335

Ile Leu Gly Lys Val Val Phe Ser Leu Thr Thr Glu Glu Lys Val Pro
            340                 345                 350

Phe Thr Phe Gly Leu Val Asp Ser Asp Gly Pro Cys Tyr Ala Val Met
        355                 360                 365

Val Tyr Asn Ile Val Gln Ser Trp Gly Val Leu Ile Gly Asp Ser Val
    370                 375                 380

Ala Ile Pro Glu Pro Asn Leu Arg Leu His Arg Ile Gln His Lys Gly
385                 390                 395                 400

Lys Asp Tyr Ser Phe Ser Ser Val Arg Val Glu Thr Pro Leu Leu Leu
                405                 410                 415

Val Val Asn Gly Lys Pro Gln Gly Ser Ser Ser Gln Ala Val Ala Thr
            420                 425                 430

Val Ala Ser Arg Pro Gln Cys Glu
        435                 440

<210> SEQ ID NO 3
<211> LENGTH: 1323
<212> TYPE: DNA
<213> ORGANISM: Mus sp.

<400> SEQUENCE: 3
atgatggctg atgaagagga agaagcgaag cacgtcttgc agaaattgca gggactggtg      60
gatcggctct actgttttcg agacagttac tttgagacac atagtgtcga agatgcagga     120
cggaagcagc aggatgtaca ggaagagatg gagaagaccc tgcagcagat ggaggaagta     180
ctcggttctg cccaggttga ggcacaggct ctgatgctga aggggaaggc actgaatgtg     240
actcctgatt atagccctga ggccgagtg cttctctcca aggccgtgaa gctggagcct     300
gagctggtgg aagcctggaa ccagctgggt gaggtgtact ggaagaaagg agatgtcaca     360
tctgcccaca cctgcttctc aggagccctc acccactgca agaacaaagt ctctctgcag     420
aacttgtcca tggtgctccg ccagctgcag accgactctg agatgaaca ttctcgccac      480 gtcatggaca gcgtccggca ggctaagttg gccgtgcaga tggatgtcct tgatggccgc     540
tcctggtata tcctggggaa tgcatatctt tctctttatt tcaatactgg ccagaaccct     600

-continued

```
aagatctccc agcaagccct cagtgcctat gctcaagcag agaaggtgga caggaaagca    660
tctagcaacc ctgaccttca tctcaacagg gcgacgttac ataaatatga ggagagttat    720
ggggaggccc ttgagggttt ctctcaggct gcagcgctgg accctgcgtg gccagagccc    780
cagcaacgag aacagcaact cttggaattc ctcagtaggc taaccagcct cctggagagc    840
aaggggaaga caaagcccaa gaagctgcag agcatgctgg gaagcttgcg cccagctcat    900
ctgggcccct gtggtgatgg cgctatcag tcggcctctg ggcagaagat gaccctggag     960
cttaagccac tgagcaccct gcagcctggt gtgaacagtg caccgtggt cctgggaaag    1020
gtggtgttca gcctgaccac agaggagaaa gtccccttca cgtttggctt ggtagattcg   1080
gatggtccct gctatgcagt gatggtgtat aatgtggtgc agagctgggg agtgctcatc   1140
ggggactctg tagctattcc tgagcccaac cttcggcatc atcaaatccg gcacaaggga   1200
aaggactatt ccttctccag cgtgcgtgtg gaaacgcctc ttctgctggt ggtgaatgga   1260
aagccacaga actccagcag tcaagcctct gccacagtag cttcaaggcc acagtgtgaa   1320
tga                                                                 1323
```

<210> SEQ ID NO 4
<211> LENGTH: 34
<212> TYPE: PRT
<213> ORGANISM: Mus sp.

<400> SEQUENCE: 4

Gln Ala Leu Met Leu Lys Gly Lys Ala Leu Asn Val Thr Pro Asp Tyr
1               5                   10                  15
Ser Pro Glu Ala Glu Val Leu Leu Ser Lys Ala Val Lys Leu Glu Pro
            20                  25                  30
Glu Leu

<210> SEQ ID NO 5
<211> LENGTH: 34
<212> TYPE: PRT
<213> ORGANISM: Mus sp.

<400> SEQUENCE: 5

Val Glu Ala Trp Asn Gln Leu Gly Glu Val Tyr Trp Lys Lys Gly Asp
1               5                   10                  15
Val Thr Ser Ala His Thr Cys Phe Ser Gly Ala Leu Thr His Cys Lys
            20                  25                  30
Asn Lys

<210> SEQ ID NO 6
<211> LENGTH: 34
<212> TYPE: PRT
<213> ORGANISM: Mus sp.

<400> SEQUENCE: 6

Gly Arg Ser Trp Tyr Ile Leu Gly Asn Ala Tyr Leu Ser Leu Tyr Phe
1               5                   10                  15
Asn Thr Gly Gln Asn Pro Lys Ile Ser Gln Gln Ala Leu Ser Ala Tyr
            20                  25                  30
Ala Gln

<210> SEQ ID NO 7
<211> LENGTH: 34
<212> TYPE: PRT

-continued

```
<213> ORGANISM: Mus sp.

<400> SEQUENCE: 7

Pro Asp Leu His Leu Asn Arg Ala Thr Leu His Lys Tyr Glu Glu Ser
 1               5                  10                  15

Tyr Gly Glu Ala Leu Glu Gly Phe Ser Gln Ala Ala Ala Leu Asp Pro
                20                  25                  30

Ala Trp

<210> SEQ ID NO 8
<211> LENGTH: 34
<212> TYPE: PRT
<213> ORGANISM: Mus sp.

<400> SEQUENCE: 8

Asn Ser Gly Thr Val Val Leu Gly Lys Val Val Phe Ser Leu Thr Thr
 1               5                  10                  15

Glu Glu Lys Val Pro Phe Thr Phe Gly Leu Val Asp Ser Asp Gly Pro
                20                  25                  30

Cys Tyr

<210> SEQ ID NO 9
<211> LENGTH: 34
<212> TYPE: PRT
<213> ORGANISM: Mus sp.

<400> SEQUENCE: 9

Val Gln Ser Trp Gly Val Leu Ile Gly Asp Ser Val Ala Ile Pro Glu
 1               5                  10                  15

Pro Asn Leu Arg His His Gln Ile Arg His Lys Gly Lys Asp Tyr Ser
                20                  25                  30

Phe Ser
```